United States Patent
Dunning et al.

(10) Patent No.: US 8,021,360 B2
(45) Date of Patent: Sep. 20, 2011

(54) SYSTEM AND METHOD FOR PROVIDING EVEN HEAT DISTRIBUTION AND COOLING RETURN PADS

(75) Inventors: James E. Dunning, Boulder, CO (US); Kyle R. Rick, Boulder, CO (US); David Gresback, Minneapolis, MN (US); Peter Gadsby, Broomfield, CO (US)

(73) Assignee: TYCO Healthcare Group LP, Boulder, CO (US)

( * ) Notice: Subject to any disclaimer, the term of this patent is extended or adjusted under 35 U.S.C. 154(b) by 1204 days.

(21) Appl. No.: 11/732,277

(22) Filed: Apr. 3, 2007

(65) Prior Publication Data

US 2008/0249520 A1    Oct. 9, 2008

(51) Int. Cl.
*A61N 1/04* (2006.01)
(52) U.S. Cl. .......................................... 606/32; 606/35
(58) Field of Classification Search ............. 606/32–52
See application file for complete search history.

(56) References Cited

U.S. PATENT DOCUMENTS

| | | |
|---|---|---|
| 2,536,271 A | 1/1951 | Fransen et al. |
| 3,380,445 A | 4/1968 | Frasier |
| 3,534,306 A | 10/1970 | Watrous et al. |
| 3,543,760 A | 12/1970 | Bolduc |
| 3,642,008 A | 2/1972 | Bolduc |
| 3,683,923 A | 8/1972 | Anderson |
| 3,812,861 A | 5/1974 | Peters |
| 3,913,583 A | 10/1975 | Bross |
| 3,923,063 A | 12/1975 | Andrews et al. |
| 3,933,157 A | 1/1976 | Bjurwill et al. |
| 3,987,796 A | 10/1976 | Gonser |
| 4,067,342 A | 1/1978 | Burton |
| 4,092,985 A | 6/1978 | Kaufman |
| 4,094,320 A | 6/1978 | Newton et al. |
| 4,102,341 A | 7/1978 | Ikuno et al. |
| 4,114,622 A | 9/1978 | Gonser |
| 4,117,846 A | 10/1978 | Williams |
| 4,121,590 A | 10/1978 | Gonser |
| 4,126,137 A | 11/1978 | Archibald |
| 4,166,465 A | 9/1979 | Esty et al. |
| 4,188,927 A | 2/1980 | Harris |
| 4,200,104 A | 4/1980 | Harris |
| 4,200,105 A | 4/1980 | Gonser |
| 4,213,463 A | 7/1980 | Osenkarski |
| 4,231,372 A | 11/1980 | Newton |
| 4,237,887 A | 12/1980 | Gosner |
| 4,253,721 A | 3/1981 | Kaufman |
| 4,303,073 A | 12/1981 | Archibald |
| 4,304,235 A | 12/1981 | Kaufman |
| 4,331,149 A | 5/1982 | Gonser |

(Continued)

FOREIGN PATENT DOCUMENTS

CA    1219642    3/1987

(Continued)

OTHER PUBLICATIONS

International Search Report EP 05021944.3 dated Jan. 25, 2006.

(Continued)

*Primary Examiner* — Linda C Dvorak
*Assistant Examiner* — Amanda Scott

(57) ABSTRACT

A return pad for use with an electrosurgical system is disclosed. The return pad includes a conductive layer, a contact layer configured to engage a patient's skin and an intermediate layer disposed between the conductive layer and the contact layer. The intermediate layer is adapted to distribute energy.

17 Claims, 13 Drawing Sheets

U.S. PATENT DOCUMENTS

| | | | | |
|---|---|---|---|---|
| 4,343,308 A | | 8/1982 | Gross | |
| 4,381,789 A | | 5/1983 | Naser et al. | |
| 4,384,582 A | | 5/1983 | Watt | |
| 4,387,714 A | | 6/1983 | Geddes et al. | |
| 4,393,584 A | | 7/1983 | Bare et al. | |
| 4,416,276 A | | 11/1983 | Newton et al. | |
| 4,416,277 A | | 11/1983 | Newton et al. | |
| 4,437,464 A | | 3/1984 | Crow | |
| 4,494,541 A | | 1/1985 | Archibald | |
| 4,643,193 A | | 2/1987 | DeMarzo | |
| 4,657,015 A | | 4/1987 | Irnich | |
| 4,658,819 A | | 4/1987 | Harris et al. | |
| 4,662,369 A | | 5/1987 | Ensslin | |
| 4,669,468 A | | 6/1987 | Cartmell et al. | |
| 4,699,146 A | | 10/1987 | Sieverding | |
| 4,722,761 A | | 2/1988 | Cartmell et al. | |
| 4,725,713 A | | 2/1988 | Lehrke | |
| 4,741,334 A | | 5/1988 | Irnich | |
| 4,745,918 A | | 5/1988 | Feucht | |
| 4,748,983 A | | 6/1988 | Shigeta et al. | |
| 4,750,482 A | | 6/1988 | Sieverding | |
| 4,754,757 A | | 7/1988 | Feucht | |
| 4,768,514 A | | 9/1988 | DeMarzo | |
| 4,770,173 A | | 9/1988 | Feucht et al. | |
| 4,788,977 A | | 12/1988 | Farin et al. | |
| 4,799,480 A | * | 1/1989 | Abraham et al. | 606/32 |
| 4,807,621 A | | 2/1989 | Hagen et al. | |
| 4,844,063 A | | 7/1989 | Clark | |
| 4,848,335 A | | 7/1989 | Manes | |
| 4,852,571 A | * | 8/1989 | Gadsby et al. | 600/396 |
| 4,862,889 A | | 9/1989 | Feucht | |
| 4,873,974 A | | 10/1989 | Hagen et al. | |
| 4,895,169 A | | 1/1990 | Heath | |
| 4,942,313 A | | 7/1990 | Kinzel | |
| 4,947,846 A | | 8/1990 | Kitagawa et al. | |
| 4,955,381 A | | 9/1990 | Way et al. | |
| 4,961,047 A | | 10/1990 | Carder | |
| 4,969,885 A | | 11/1990 | Farin | |
| 5,000,753 A | | 3/1991 | Hagen et al. | |
| 5,004,425 A | | 4/1991 | Hee | |
| 5,010,896 A | | 4/1991 | Westbrook | |
| 5,038,796 A | | 8/1991 | Axelgaard et al. | |
| 5,042,981 A | | 8/1991 | Gross | |
| 5,061,914 A | | 10/1991 | Busch et al. | |
| 5,087,257 A | | 2/1992 | Farin | |
| 5,114,424 A | | 5/1992 | Hagen et al. | |
| 5,152,762 A | | 10/1992 | McElhenney | |
| 5,160,334 A | | 11/1992 | Billings et al. | |
| 5,196,008 A | | 3/1993 | Kuenecke | |
| 5,246,439 A | | 9/1993 | Hebborn et al. | |
| 5,271,417 A | | 12/1993 | Swanson et al. | |
| 5,276,079 A | | 1/1994 | Duan et al. | |
| 5,286,255 A | | 2/1994 | Weber | |
| 5,312,401 A | | 5/1994 | Newton et al. | |
| 5,336,255 A | | 8/1994 | Kanare et al. | |
| 5,352,315 A | | 10/1994 | Carrier et al. | |
| 5,362,420 A | | 11/1994 | Itoh et al. | |
| 5,370,645 A | | 12/1994 | Klicek et al. | |
| 5,385,679 A | | 1/1995 | Uy et al. | |
| 5,388,490 A | | 2/1995 | Buck | |
| 5,389,376 A | | 2/1995 | Duan et al. | |
| 5,390,382 A | | 2/1995 | Hannant et al. | |
| 5,409,966 A | | 4/1995 | Duan et al. | |
| 5,447,513 A | | 9/1995 | Davison et al. | |
| 5,449,365 A | | 9/1995 | Green et al. | |
| 5,452,725 A | | 9/1995 | Martenson | |
| 5,480,399 A | | 1/1996 | Hebborn | |
| 5,496,312 A | | 3/1996 | Klicek | |
| 5,496,363 A | | 3/1996 | Burgio et al. | |
| 5,520,180 A | | 5/1996 | Uy et al. | |
| 5,536,446 A | | 7/1996 | Uy et al. | |
| 5,540,684 A | | 7/1996 | Hassler, Jr. | |
| 5,599,347 A | | 2/1997 | Hart et al. | |
| 5,601,618 A | | 2/1997 | James | |
| 5,611,709 A | | 3/1997 | McAnulty | |
| 5,632,280 A | | 5/1997 | Leyde et al. | |
| 5,643,319 A | | 7/1997 | Green et al. | |
| 5,660,892 A | | 8/1997 | Robbins et al. | |
| 5,670,557 A | | 9/1997 | Dietz et al. | |
| 5,674,561 A | | 10/1997 | Dietz et al. | |
| 5,678,545 A | | 10/1997 | Stratbucker | |
| 5,688,269 A | | 11/1997 | Newton et al. | |
| 5,695,494 A | | 12/1997 | Becker | |
| 5,707,369 A | | 1/1998 | Vaitekunas et al. | |
| 5,718,719 A | | 2/1998 | Clare et al. | |
| 5,720,744 A | | 2/1998 | Eggleston et al. | |
| 5,766,165 A | | 6/1998 | Gentelia et al. | |
| 5,779,632 A | | 7/1998 | Dietz et al. | |
| 5,797,902 A | | 8/1998 | Netherly | |
| 5,800,426 A | | 9/1998 | Taki et al. | |
| 5,817,091 A | | 10/1998 | Nardella et al. | |
| 5,830,212 A | | 11/1998 | Cartmell et al. | |
| 5,836,942 A | | 11/1998 | Netherly et al. | |
| 5,846,558 A | | 12/1998 | Nielsen et al. | |
| 5,853,750 A | | 12/1998 | Dietz et al. | |
| 5,868,742 A | | 2/1999 | Manes et al. | |
| 5,924,983 A | | 7/1999 | Takaki et al. | |
| 5,947,961 A | | 9/1999 | Netherly | |
| 5,952,398 A | | 9/1999 | Dietz et al. | |
| 5,971,981 A | | 10/1999 | Hill et al. | |
| 5,976,128 A | | 11/1999 | Schilling et al. | |
| 5,985,990 A | | 11/1999 | Kantner et al. | |
| 5,999,061 A | | 12/1999 | Pope et al. | |
| 6,007,532 A | | 12/1999 | Netherly | |
| 6,010,054 A | | 1/2000 | Johnson et al. | |
| 6,030,381 A | | 2/2000 | Jones et al. | |
| 6,032,063 A | | 2/2000 | Hoar et al. | |
| 6,039,732 A | | 3/2000 | Ichikawa et al. | |
| 6,053,910 A | | 4/2000 | Fleenor | |
| RE36,720 E | | 5/2000 | Green et al. | |
| 6,059,778 A | | 5/2000 | Sherman | |
| 6,063,075 A | | 5/2000 | Mihori | |
| 6,083,221 A | | 7/2000 | Fleenor et al. | |
| 6,086,249 A | | 7/2000 | Urich | |
| 6,121,508 A | | 9/2000 | Bischof et al. | |
| 6,135,953 A | | 10/2000 | Carim | |
| 6,171,304 B1 | | 1/2001 | Netherly et al. | |
| 6,200,314 B1 | | 3/2001 | Sherman | |
| 6,203,541 B1 | | 3/2001 | Keppel | |
| 6,214,000 B1 | | 4/2001 | Fleenor et al. | |
| 6,232,366 B1 | | 5/2001 | Wang et al. | |
| 6,240,323 B1 | | 5/2001 | Calenzo, Sr. et al. | |
| 6,258,085 B1 | | 7/2001 | Eggleston | |
| 6,275,786 B1 | | 8/2001 | Daners | |
| 6,283,987 B1 | * | 9/2001 | Laird et al. | 607/96 |
| 6,301,500 B1 | | 10/2001 | Van Herk et al. | |
| 6,310,611 B1 | | 10/2001 | Caldwell | |
| 6,347,246 B1 | | 2/2002 | Perrault et al. | |
| 6,350,264 B1 | | 2/2002 | Hooven | |
| 6,356,779 B1 | * | 3/2002 | Katzenmaier et al. | 600/391 |
| 6,357,089 B1 | | 3/2002 | Koguchi et al. | |
| 6,358,245 B1 | | 3/2002 | Edwards et al. | |
| 6,379,161 B1 | | 4/2002 | Ma | |
| 6,409,722 B1 | | 6/2002 | Hoey et al. | |
| 6,413,255 B1 | | 7/2002 | Stern | |
| 6,415,170 B1 | | 7/2002 | Loutis et al. | |
| 6,454,764 B1 | | 9/2002 | Fleenor et al. | |
| 6,488,678 B2 | | 12/2002 | Sherman | |
| 6,537,272 B2 | | 3/2003 | Christopherson et al. | |
| 6,544,258 B2 | * | 4/2003 | Fleenor et al. | 606/32 |
| 6,546,270 B1 | | 4/2003 | Goldin et al. | |
| 6,565,559 B2 | | 5/2003 | Eggleston | |
| 6,569,160 B1 | | 5/2003 | Goldin et al. | |
| 6,582,424 B2 | | 6/2003 | Fleenor et al. | |
| 6,666,859 B1 | | 12/2003 | Fleenor et al. | |
| 6,669,073 B2 | | 12/2003 | Milliman et al. | |
| 6,736,810 B2 | | 5/2004 | Hoey et al. | |
| 6,796,828 B2 | | 9/2004 | Ehr et al. | |
| 6,799,063 B2 | * | 9/2004 | Carson | 600/372 |
| 6,830,569 B2 | | 12/2004 | Thompson et al. | |
| 6,849,073 B2 | | 2/2005 | Hoey et al. | |
| 6,860,881 B2 | | 3/2005 | Sturm | |
| 6,875,210 B2 | | 4/2005 | Refior et al. | |
| 6,892,086 B2 | | 5/2005 | Russell | |
| 6,905,497 B2 | | 6/2005 | Truckai et al. | |
| 6,939,344 B2 | | 9/2005 | Kreindel | |
| 6,948,503 B2 | | 9/2005 | Refior et al. | |

| | | | | | |
|---|---|---|---|---|---|
| 6,953,139 B2 | 10/2005 | Milliman et al. | EP | 390937 | 10/1990 |
| 6,959,852 B2 | 11/2005 | Shelton, IV et al. | EP | 836868 | 4/1998 |
| 6,997,735 B2 | 2/2006 | Ehr et al. | EP | 0 930 048 | 7/1999 |
| 7,025,765 B2 | 4/2006 | Balbierz et al. | EP | 1 051 949 | 11/2000 |
| 7,128,253 B2 | 10/2006 | Mastri et al. | EP | 1076350 | 2/2001 |
| 7,143,926 B2 | 12/2006 | Shelton, IV et al. | EP | 1 468 653 | 10/2004 |
| 7,160,293 B2 | 1/2007 | Sturm et al. | EP | 1 645 236 | 4/2006 |
| 7,166,102 B2 | 1/2007 | Fleenor et al. | EP | 1707151 | 10/2006 |
| 7,169,144 B2 | 1/2007 | Hoey et al. | EP | 1 808 144 | 7/2007 |
| 7,169,145 B2 | 1/2007 | Isaacson et al. | EP | 1902684 | 3/2008 |
| 7,182,604 B2 | 2/2007 | Ehr et al. | FR | 2276027 | 6/1974 |
| 7,220,260 B2 | 5/2007 | Fleming et al. | FR | 2516782 | 5/1983 |
| 7,229,307 B2 | 6/2007 | Ehr et al. | GB | 2 054 382 | 2/1981 |
| 7,258,262 B2 | 8/2007 | Mastri et al. | GB | 2374532 | 10/2002 |
| 7,267,675 B2 | 9/2007 | Stern et al. | WO | WO 96/19152 | 6/1996 |
| 7,278,562 B2 | 10/2007 | Mastri et al. | WO | WO 97/37719 | 10/1997 |
| 7,303,107 B2 | 12/2007 | Milliman et al. | WO | WO 98/18395 | 5/1998 |
| 7,308,998 B2 | 12/2007 | Mastri et al. | WO | WO 98/53751 | 12/1998 |
| 7,311,560 B2 | 12/2007 | Ehr et al. | WO | WO 99/09899 | 3/1999 |
| 7,357,287 B2 | 4/2008 | Shelton, IV et al. | WO | WO 99/11187 | 3/1999 |
| 7,380,695 B2 | 6/2008 | Doll et al. | WO | WO 00/06246 | 2/2000 |
| 7,422,589 B2 | 9/2008 | Newton et al. | WO | WO 00/32122 | 6/2000 |
| 7,473,145 B2 | 1/2009 | Ehr et al. | WO | WO 00/53113 | 9/2000 |
| 2003/0139741 A1 | 7/2003 | Goble et al. | WO | WO 00/65993 | 11/2000 |
| 2003/0171748 A1* | 9/2003 | Truckai et al. ............. 606/51 | WO | WO 01/87175 | 11/2001 |
| 2003/0216728 A1* | 11/2003 | Stern et al. ............. 606/41 | WO | WO 02/058579 | 8/2002 |
| 2004/0150504 A1 | 8/2004 | Nicholson | WO | WO 02/060526 | 8/2002 |
| 2005/0021022 A1 | 1/2005 | Sturm et al. | WO | WO 02/099442 | 12/2002 |
| 2005/0079752 A1 | 4/2005 | Ehr et al. | WO | WO 03/094766 | 11/2003 |
| 2005/0085806 A1 | 4/2005 | Auge, II et al. | WO | WO 2004/028385 | 4/2004 |
| 2005/0101947 A1 | 5/2005 | Jarrard et al. | WO | WO 2004/074854 | 9/2004 |
| 2005/0251130 A1 | 11/2005 | Boveja et al. | WO | WO 2005/048809 | 6/2005 |
| 2006/0030195 A1 | 2/2006 | Ehr et al. | WO | WO 2005/087124 | 9/2005 |
| 2006/0041251 A1 | 2/2006 | Odell et al. | WO | WO 2005/099606 | 10/2005 |
| 2006/0041252 A1 | 2/2006 | Odell et al. | WO | WO 2005/110263 | 11/2005 |
| 2006/0041253 A1 | 2/2006 | Newton et al. | WO | WO 2005/115262 | 12/2005 |
| 2006/0074411 A1 | 4/2006 | Carmel et al. | WO | WO 2008/009385 | 1/2008 |
| 2006/0079872 A1 | 4/2006 | Eggleston | | | |
| 2006/0173250 A1 | 8/2006 | Nessler | | | |
| 2006/0217742 A1 | 9/2006 | Messerly et al. | | | |
| 2006/0224150 A1 | 10/2006 | Arts et al. | | | |
| 2007/0049914 A1 | 3/2007 | Eggleston | | | |
| 2007/0049916 A1 | 3/2007 | Isaacson et al. | | | |
| 2007/0049919 A1 | 3/2007 | Lee, Jr. et al. | | | |
| 2007/0073284 A1 | 3/2007 | Sturm | | | |
| 2007/0074719 A1 | 4/2007 | Danek et al. | | | |
| 2007/0161979 A1 | 7/2007 | McPherson | | | |
| 2007/0167942 A1 | 7/2007 | Rick | | | |
| 2007/0203481 A1 | 8/2007 | Gregg et al. | | | |
| 2007/0244478 A1 | 10/2007 | Bahney | | | |
| 2008/0009846 A1 | 1/2008 | Ward | | | |
| 2008/0033276 A1 | 2/2008 | Ehr et al. | | | |
| 2008/0083806 A1 | 4/2008 | Scirica | | | |
| 2008/0083813 A1 | 4/2008 | Zemlok et al. | | | |
| 2008/0249520 A1 | 10/2008 | Dunning et al. | | | |
| 2008/0249524 A1 | 10/2008 | Dunning | | | |
| 2008/0281309 A1 | 11/2008 | Dunning et al. | | | |
| 2008/0281310 A1 | 11/2008 | Dunning et al. | | | |
| 2008/0281311 A1 | 11/2008 | Dunning et al. | | | |
| 2009/0036884 A1 | 2/2009 | Gregg et al. | | | |
| 2009/0036885 A1 | 2/2009 | Gregg | | | |

FOREIGN PATENT DOCUMENTS

| | | |
|---|---|---|
| DE | 3206947 | 9/1983 |
| DE | 3544443 | 6/1987 |
| DE | 42 38 263 A1 | 5/1993 |
| DE | 4231236 | 3/1994 |
| DE | 197 17 411 A1 | 11/1998 |
| DE | 198 01 173 | 7/1999 |
| DE | 103 28 514 | 6/2003 |
| DE | 102004010940 | 9/2005 |
| EP | 0262888 | 4/1988 |

OTHER PUBLICATIONS

International Search Report EP 05002027.0 dated May 12, 2005.
International Search Report EP 06006961 dated Aug. 3, 2006.
International Search Report EP 07000885.9 dated May 15, 2007.
International Search Report EP07000567.3 dated Dec. 3, 2008.
International Search Report EP08006731 dated Jul. 14, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779-partial dated Sep. 8, 2008.
International Search Report EP08155779 dated Jan. 23, 2009.
International Search Report EP09152032 dated Jun. 17, 2009.
International Search Report EP09152130.2 dated Apr. 6, 2009.
Boyles, Walt; "Instrumentation Reference Book", 2002; Butterworth-Heinemann ; 262-264.
International Search Report EP06023756.7 dated Feb. 21, 2008.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report PCT/US2004/004196 dated Oct. 4, 2007.
International Search Report EP06006961.4 dated Oct. 5, 2007.
International Search Report EP07000885.9 dated May 2, 2007.
International Search Report EP07007783.9 dated Aug. 6, 2007.
International Search Report EP06018206.0 dated Oct. 13, 2006.

* cited by examiner

SYSTEM AND METHOD FOR PROVIDING EVEN HEAT DISTRIBUTION AND COOLING RETURN PADS

BACKGROUND

1. Technical Field

The present disclosure is directed to electrosurgical apparatus, methods and systems, and, in particular, to an electrosurgical return pad that provides even heat and current distribution and cooling.

2. Background of Related Art

During monopolar electrosurgery, a source or active electrode delivers energy, such as radio frequency energy, from an electrosurgical generator to the patient and a return pad carries the current back to the electrosurgical generator. The source electrode is typically placed at the surgical site and high density current flows from the source electrode to create the desired surgical effect of cutting and/or coagulating tissue. In tissue ablation, another form of electrosurgery, the source electrode or electrodes are typically placed in or adjacent the target tissue and high density current flows through the target tissue thereby destroying the target tissue. The patient return pad is placed at a distance from the source electrode and may be in the form of a pad adhesively adhered to the patient.

The return pad typically has a large patient contact surface area to minimize heating at that return pad site. The larger the contact area between the return pad and patient skin, the lower the current density and the lower the intensity of the heat. The size of return pads is based on assumptions of the maximum current seen in surgery and the duty cycle (e.g., the percentage of time the generator is on) during the procedure. The first types of return pads were in the form of large metal plates covered with conductive jelly. Later, adhesive electrodes were developed with a single metal foil covered with contact layer formed of conductive jelly, conductive adhesive or conductive hydrogel.

One issue with these adhesive electrodes was that current flow from the active electrode concentrates at the leading edge, the edge of the return pad closest to the active electrode, causing a heating imbalance across the return pad. This phenomenon, known as "Leading Edge Effect" can cause tissue change or injury if the skin under the leading edge portion of the return pad is heated beyond the point where circulation of blood can cool the skin.

SUMMARY

The present disclosure relates to an electrosurgical return pad. The return pad, for use in performing electrosurgical procedures, includes a conductive layer, a contact layer configured to engage a patient's skin and an intermediate layer disposed between the conductive layer and the adhesive layer. The intermediate layer is adapted to distribute energy.

The intermediate layer is constructed from a material that may include a dielectric layer, a carbon layer, evaporative layer or any combination thereof. The material of the intermediate layer may be silk screened or printed onto the conductive layer, or vice-versa. Intermediate layer and the conductive layer may be joined by a conductive adhesive, such as a hydrogel. The impedance of the material may be configured to be substantially uniform or the impedance may decrease away from a leading edge of the return pad.

The contact layer may include a plurality of contact layer sections and an insulating barrier between each of the plurality of contact layer sections.

The conductive layer may be is disposed on a portion of the intermediate section and may be spaced away from the leading edge of the intermediate layer. A backing layer may be at least partially disposed on the conductive layer.

Intermediate layer may include a cooling device selected from an active cooling device and a passive cooling device. Alternatively, intermediate layer may include at least one cooling chamber configured to allow fluid to flow therethrough.

In yet another embodiment of the present disclosure return pad is disclosed that includes a conductive layer and a contact layer. The contact layer is disposed on the conductive layer and is configured to engage patient skin. A cooling section may be disposed on the conductive layer and configured to reduce the temperature of at least one of the contact layer and the conductive layer.

The cooling section may include a heat exchanger, an evaporative material, a passive cooling device, a Peltier cooling device and/or a heat exchanger. A backing layer may be disposed on the cooling section and may be adapted to allow heat to dissipate therethrough. Alternatively, cooling section may include at least one cooling chamber configured to allow fluid to flow therethrough.

Cooling section may further include an intermediate layer disposed on the conductive layer and constructed from a material that distributes energy. The cooling section may also include a cooling device disposed on the intermediate layer that may consist of an active cooling device, a passive cooling device and/or may include an evaporative material. A backing material may be at least partially disposed on the cooling device. The intermediate layer may be a dielectric layer and/or a carbon layer.

In yet another embodiment of the present disclosure a return pad is disclosed that includes a cooling system for electrosurgical surgery having a return pad and a cooling system for supplying cooling fluid. The return pad includes a conductive layer, a contact layer disposed on the conductive layer and configured to engage patient skin and a cooling section. The cooling section may be disposed on the conductive layer and configured to reduce the temperature of the contact layer and/or the conductive layer. The cooling section may include one or more cooling chambers configured to allow fluid to flow therethrough. The cooling system is configured to supply cooling fluid to the cooling chamber and may include a pump that circulates cooling fluid through the cooling chamber. Cooling section may also include an intermediate layer disposed on the conductive layer that is configured to distribute energy.

In yet another embodiment of the present disclosure a method for performing electrosurgery is disclosed and includes the steps of: providing an electrosurgical return pad including a conductive layer, a contact layer configured to engage patient skin and an intermediate layer disposed between the conductive layer and the contact layer. The intermediate layer is adapted to distribute energy. The method also includes the steps of: placing the electrosurgical return pad in contact with patient skin; generating electrosurgical energy via an electrosurgical generator; and supplying the electrosurgical energy to the patient via an active electrode. The intermediate layer may include a dielectric layer, a carbon layer and/or an evaporative layer.

The method for performing monopolar surgery may include a cooling device and further include the step of enabling the cooling device.

BRIEF DESCRIPTION OF THE DRAWINGS

The above and other aspects and features of the present disclosure will become more apparent in light of the following detailed description when taken in conjunction with the accompanying drawings in which.

DETAILED DESCRIPTION

Figure 1A:
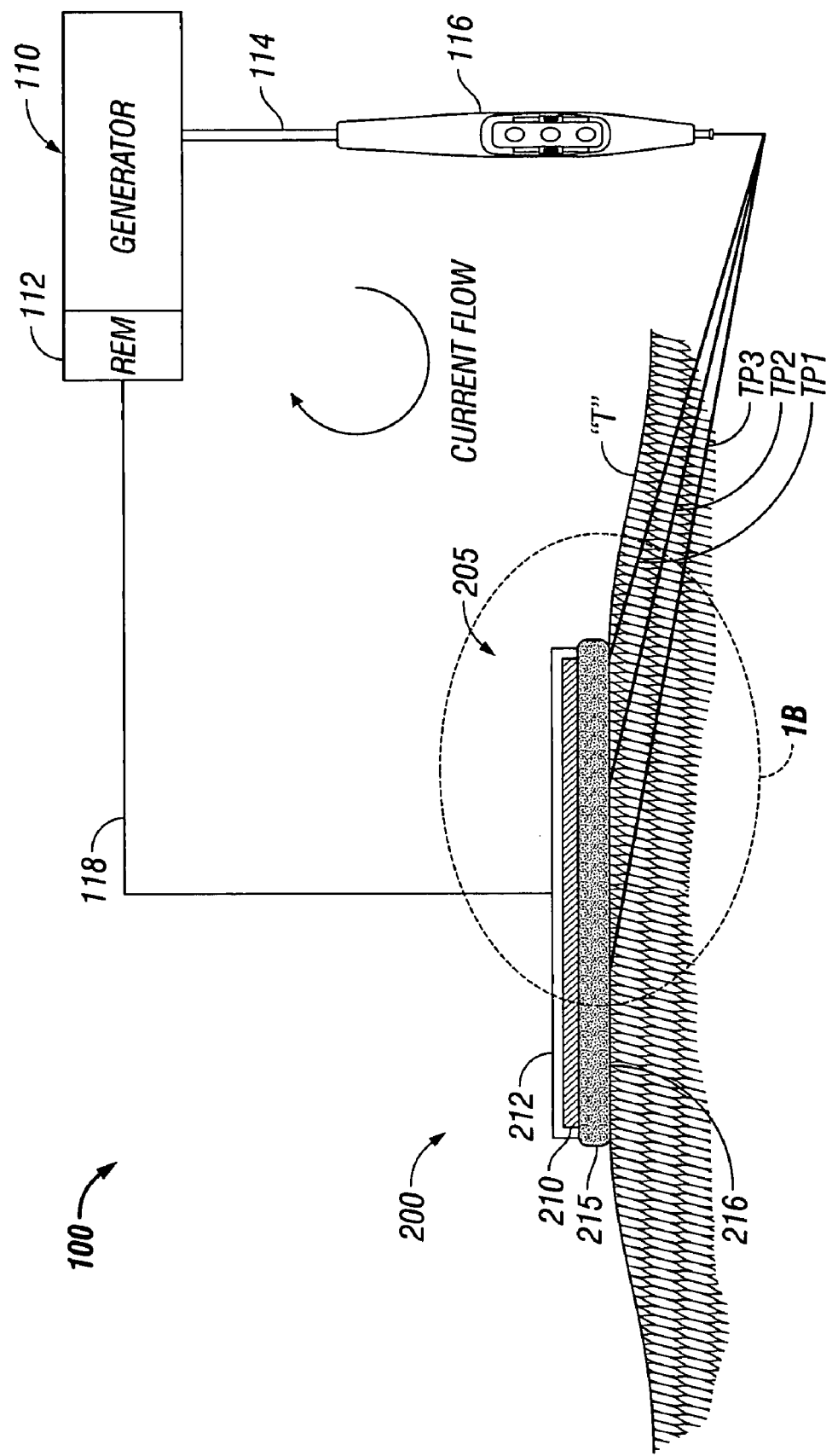
FIG. 1A is a schematic illustration of a monopolar electrosurgical system with a return pad.

Embodiments of the presently-disclosed electrosurgical return electrode (return pad) and method of using the same are described below with reference to the accompanying drawing figures wherein like reference numerals identify similar or identical elements. In the following description, well-known functions or constructions are not described in detail to avoid obscuring the disclosure in unnecessary detail. In addition, terms such as "above", "below", "forward", "rearward", etc. refer to the orientation of the figures or the direction of components and are simply used for convenience of description.

Heat Distribution

Referring initially to FIG. 1A, a schematic illustration of a monopolar electrosurgical system 100 is shown. The electrosurgical system 100 generally includes a return pad 200, an electrosurgical generator 110, a surgical instrument 116 (e.g., an active electrode) and a return electrode monitor (REM) 112. In FIG. 1A and in the figures hereinbelow, return pad 200 is illustrated in contact with patient tissue "T". Generally, electrosurgical energy is supplied to the active electrode 116 by the generator 110 through a supply cable 114 to treat tissue (e.g., cut, coagulate, blend, etc.). The return pad 200 acts as a return path for energy delivered by the active electrode 116 to patient tissue "T". Energy returns back to the electrosurgical generator 110 via a return cable 118.

While FIGS. 1A-9 depict cross-sections of return pads 200, 300, 400, 500, 600, 600a-d, 700 and 800, it is within the scope of the disclosure for the return pads to have any suitable regular or irregular shape.

Figure 1B:
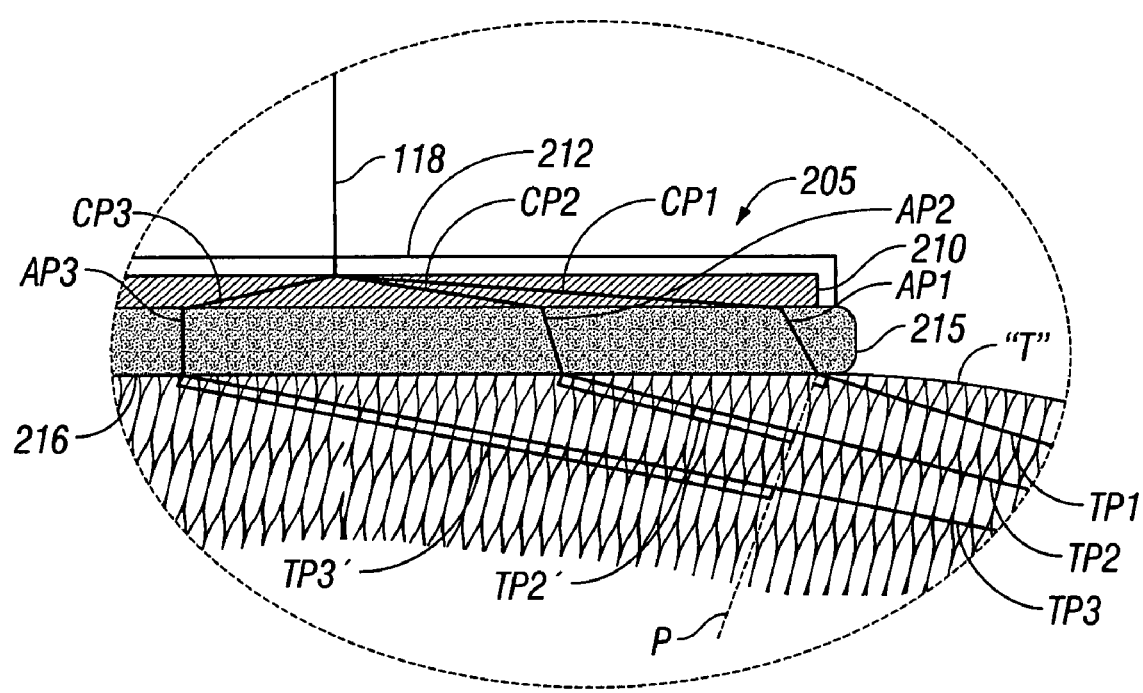
FIG. 1B is a detail of the leading edge of the return pad of FIG. 1.

In the embodiments illustrated in FIGS. 1A and 1B, return pad 200 is formed of a conductive layer 210 engaged on the top with an insulating layer 212 and on the bottom with a contact layer 215. Conductive layer 210 connects to generator 110 by return cable 118 in any suitable manner.

Contact layer 215 is formed of a gel or adhesive configured to couple to patient tissue "T" and can be made from, but is not limited to, a polyhesive adhesive, conductive hydrogel, a Z-axis adhesive or a water-insoluble, hydrophilic, pressure-sensitive adhesive. The portion of the contact layer 215 in contact with a patient tissue "T" is a patient-contacting surface 216 that is configured to ensure an optimal contact area between the return pad 200 and the patient tissue "T". In addition, contact layer 215 provides ionic conductive contact with the skin to transfer energy out of the body.

A leading edge 205 of the return pad 200 is that portion of the return pad 200 positioned closest to the active electrode 116. Leading edge 205 is defined in this disclosure not as a single point but as a general portion of the return pad 200 positioned closest to the active electrode 116.

In use, the current applied by the active electrode 116 travels through various tissue paths between the active electrode 116 and the return pad 200. The amount of current supplied by the active electrode 116 is typically equal to the amount of current received by the return pad 200. The only difference between the active electrode 116 and the return pad 200 is the amount of area in which the current is conducted. Concentration of electrons at the active electrode 116 is high due to the small surface area of the active electrode 116, which results in high current density and generation of heat, while the large surface area of the return pad 200 disperses the same current over the large contacting surface 216 resulting in a low current density and little production of heat.

Electric charge passing between the active electrode 116 and the return pad 200 will travel along various paths in patient tissue "T" and will seek the path with the lowest impedance. With reference to FIGS. 1A-4, three tissue paths (TP1), (TP2) and (TP3) are provided for illustrating tissue paths with varying impedances. However, any number of suitable paths may be utilized for conducting current through tissue "T".

Tissue path one (TP1) is a path in patient tissue "T" between the active electrode 116 and the leading edge 205 of return pad 200. Tissue path two (TP2) and tissue path three (TP3) are paths in patient tissue "T" between the active electrode 116 and a portion of the return pad 200 away from the leading edge 205 of the return pad 200.

The total impedance of a given pathway between the active electrode 116 and the return cable 118, through the return pad 200, is determined by combining the impedance of the tissue pathway and the impedance of the various layers of the return pad 200. As illustrated in FIG. 1B, the impedance of the first path equals the sum of the impedance of the first tissue path (TP1), the impedance of the first adhesive path (AP1) through the contact layer 215 and the impedance of the first conductive path (CP1) through the conductive layer 220. Similarly, the impedance of the second path equals the sum of the impedance of the second tissue path (TP2), the impedance of the second adhesive path (AP2) and the impedance of the second conductive path (CP2). Finally, impedance of the third path equals the sum of the impedance of the third tissue path (TP3), the impedance of the third adhesive path (AP3) and the impedance of the third conductive path (CP3).

In comparing the impedance of the various portions of the three illustrative current pathways, the impedance of adhesive paths (AP1), (AP2) and (AP3) and the impedance of conductive paths (CP1), (CP2) and (CP3) are substantially the same regardless of the tissue path selected. In addition, the impedance of adhesive path (AP1), (AP2) and AP3 and the impedance of a conductive path (CP1), (CP2) and (CP3) are generally small in comparison to the impedance of a tissue path (TP1), (TP3) and (TP3) and are therefore negligible with respect to the impedance of each respective tissue path (TP1), (TP2) and (TP3). Therefore, the current density at any point on the contacting surface 216 is generally dependant on the impedance of the tissue path.

As illustrated by perpendicular "P" drawn from first tissue path (TP1) in FIG. 1B, the lengths of the second and third tissue paths (TP2) and (TP3) are longer than first tissue path (TP1) by lengths of (TP2') and (TP3'), respectively. This additional length (TP2') and (TP3') in tissue adds additional impedance to second and third tissue paths (TP2) and (TP3), thus resulting in a higher current density at the leading edge 205 and a reduction in current density away from leading edge 205.

This phenomenon, known as "Leading Edge Effect," results in the concentration of energy and heat at the leading edge 205 of the return pad 200 and heating imbalance across the return pad 200. Leading Edge Effect may result in serious injury to skin under the leading edge 205 if patient tissue "T" is heated beyond the point where circulation of blood can cool the tissue.

Figure 2A:
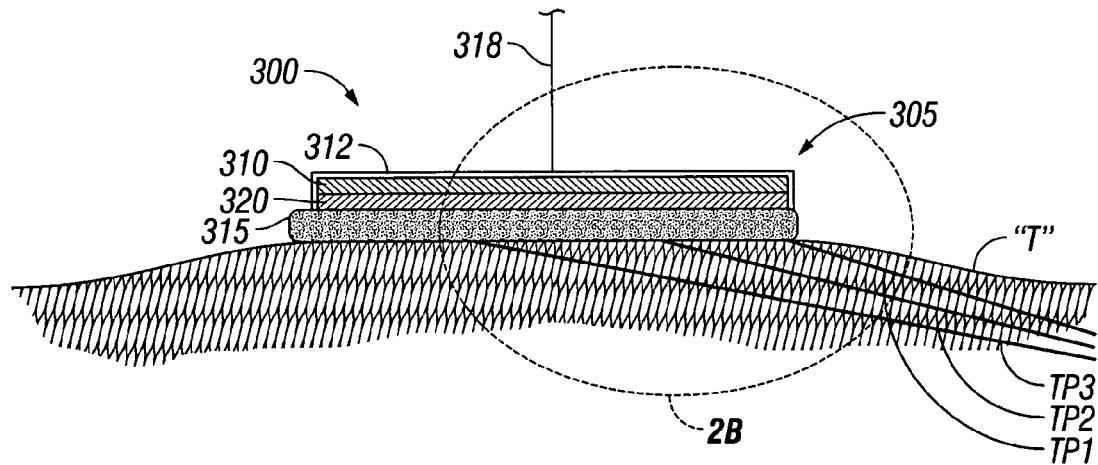
FIG. 2A is a cross-sectional view of one envisioned construction of a return pad with an intermediate layer of the present disclosure.

FIG. 2A is a cross-sectional view of a first embodiment of the present disclosure. Return pad 300 for providing, among other advantages, even heat distribution is formed of a conductive layer 310, an insulating layer 312 disposed on conductive layer 310, and an intermediate layer 320 placed between conductive layer 310 and contact layer 315. In one embodiment, intermediate layer 320 is formed of a thin dielectric material, such as, for example, a polyimide film sold under the trademark Kapton™ or a biaxially-oriented polyethylene terephthalate polyester film sold under the trademark Mylar™. In other embodiments, intermediate layer 320 may also be formed of a semi-conductive material, such as, for example, carbon, silicon, or germanium.

Intermediate layer 320 forms a low impedance connection with conductive layer 310 and contact layer 315. Low impedance connection may be formed by printing or silk screening the intermediate layer 320 on conductive layer 310. Alternatively, conductive layer 310 may be printed or silk screened on intermediate layer 320. Low impedance connection may be formed by bonding conductive layer 310 and intermediate layer 320 with a suitable conductive adhesive or gel. Such conductive adhesive or gel can be made from, but is not limited to, a polyhesive adhesive, conductive hydrogel, a Z-axis adhesive or a water-insoluble, hydrophilic, pressure-sensitive adhesive. Contact layer 315 forms a low impedance connection with intermediate layer 320.

Figure 2B:
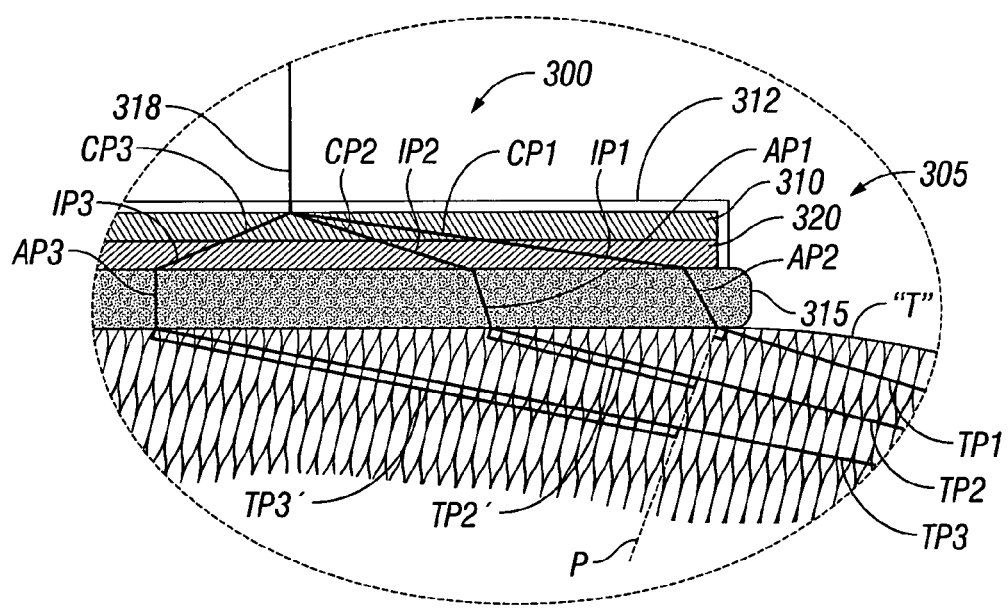
FIG. 2B is a cross-sectional detail of the leading edge of the return pad of FIG. 2.

With additional reference to FIG. 2B, the total impedance for a given pathway between the active electrode (not explicitly shown) and a return cable 318, through the return pad 300, includes the respective sum of the impedance of the tissue path (TP1), (TP2) and (TP3), the impedance of the adhesive paths (AP1), (AP2) and (AP3), the impedance of the conductive paths (CP1), (CP2) and (CP3) and the impedance of the intermediate path (IP1), (IP2) and (IP3). The additional impedance of the intermediate layer 320 evenly distributes the current flow through the return pad 300, thus reducing the current density at the leading edge 305 of return pad 300 or leading edge 305 of contact layer 315.

Intermediate layer 320 may also conduct heat generated by the current flowing through patient tissue "T" and the return pad 300. Areas of higher current density may generate hot spots on the return pad 300. Intermediate layer 320 evenly distributes energy, i.e. heat and/or current, thus lowering the temperature of hot spots on the return pad 300.

The impedance of the intermediate layer 320 may not be uniform. Intermediate layer 320 may have greater impedance at leading edge 305 of return pad 300 and the impedance of the intermediate layer 320 may be reduced away from the leading edge 305. For example, the impedance of the first intermediate path (IP1) may be greater than the impedance of the second intermediate path (IP2), and the impedance of the third intermediate path (IP3) may be less than the impedance of first and second intermediate paths (IP1) and (IP2). Reduction in impedance of the intermediate layer 320 away from leading edge 305 may be gradual, linear or non-linear. The change in impedance may be accomplished by changing the material type, material density, material construction or any other suitable method or means for varying material impedance.

The varying impedance of the intermediate layer 320 may offset the difference in impedance of the various tissue pathways (TP1), (TP2) and (TP3). As discussed hereinabove, the perpendicular "P" from the first tissue pathway (TP1) illustrates the additional impedance lengths of the second and third tissue pathway (TP2') and (TP3'). Varying the impedance of the intermediate layer 320 may equalize the impedance of the three illustrative pathways. For example, the impedance of the first and third illustrative pathways will be substantially the same if the sum of the impedance in tissue of (TP3') and the impedance of the third intermediate path (IP3) equal the impedance of the first intermediate path (IP1). Similarly, the impedance of the first and second illustrative pathways will be equal if the sum of the impedance in tissue of (TP2') and the impedance of the second intermediate path (IP2) equal the impedance of the first intermediate path (IP1).

Figure 3A:
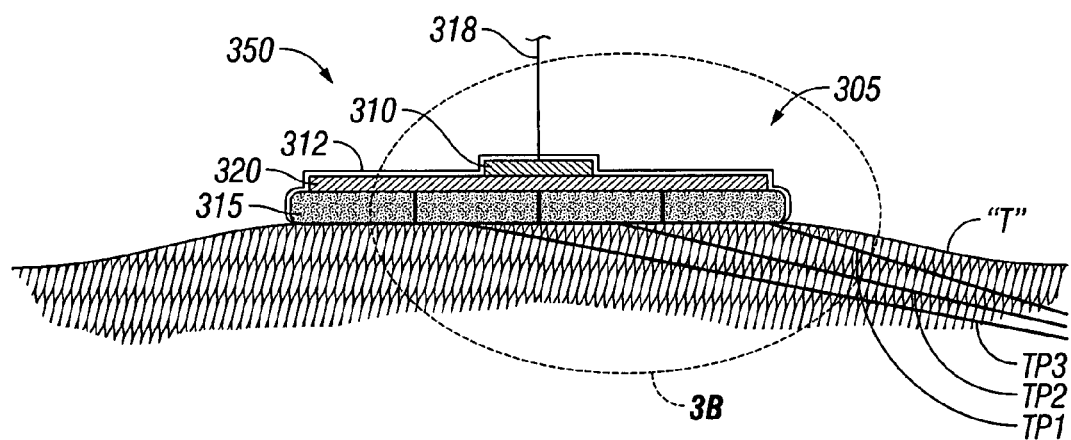
FIG. 3A is a cross-sectional view of yet another embodiment of a return pad having an intermediate layer disposed between a conductive layer and a first contact layer.
Figure 3B:
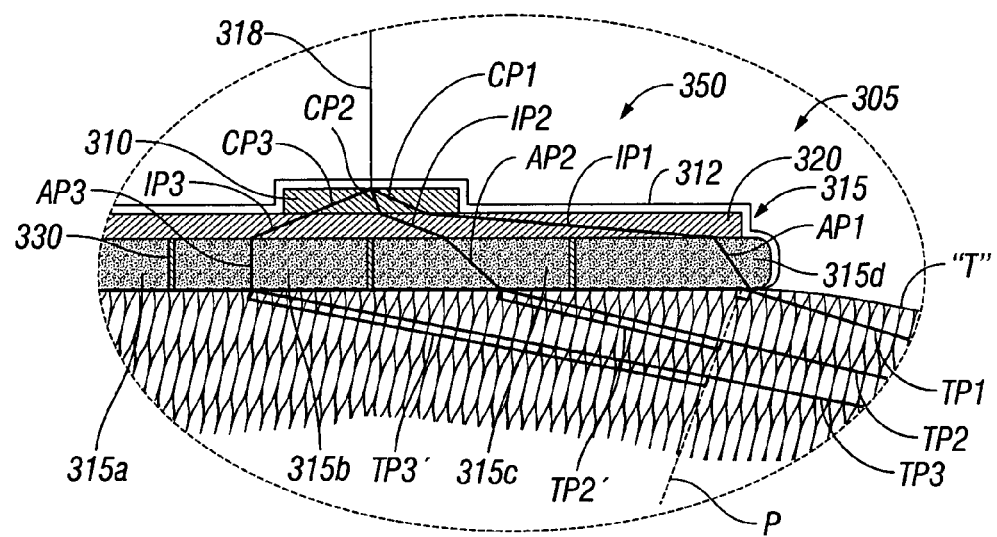
FIG. 3B is a cross-sectional detail of the leading edge of the return pad of FIG. 3.

Referring now to FIGS. 3A and 3B, a return pad 350 for providing, among other advantages, even heat distribution is shown and includes a conductive layer 310, an intermediate layer 320 and contact layer 315 larger than conductive layer 310. Return cable 318 connects to conductive layer 310. Insulating layer 312 is disposed upon at least a portion of the conductive layer 310 and the intermediate layer 320. Reduction in the size of the conductive layer 310 relative to intermediate layer 320 and contact layer 315 increases the impedance of current pathways away from the conductive layer 310.

With reference to FIGS. 2A and 3A, reducing the size of the conductive layer 310, as illustrated in FIG. 3B, does not change the impedance of the second intermediate path (IP2) because the pathway in the two embodiments is unchanged. The reduction of the size of the conductive layer 310 increases the impedance of the first intermediate path (IP1) because the conductive layer is spaced a distance away from the leading edge 305 while the impedance of the third intermediate path (IP3) is slightly increased.

Figure 4A:
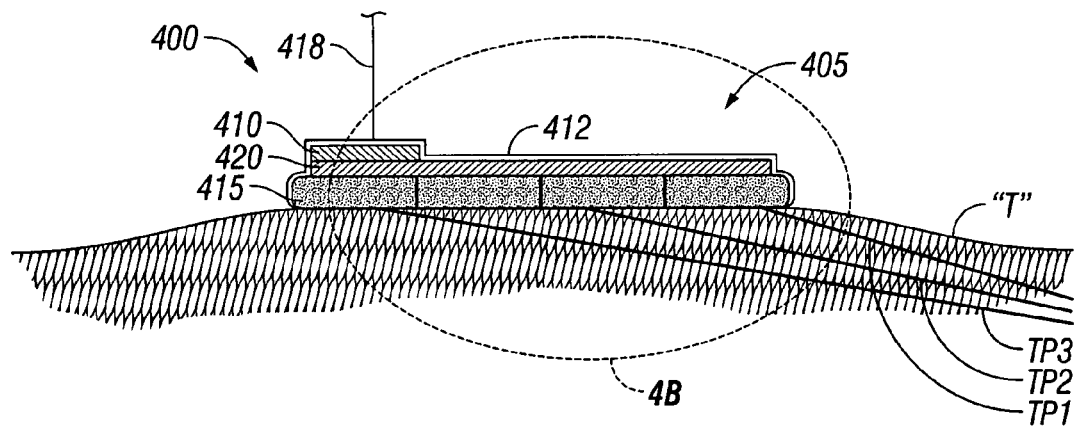
FIG. 4A is a cross-sectional view of yet another embodiment of a return pad with an intermediate layer.
Figure 4B:
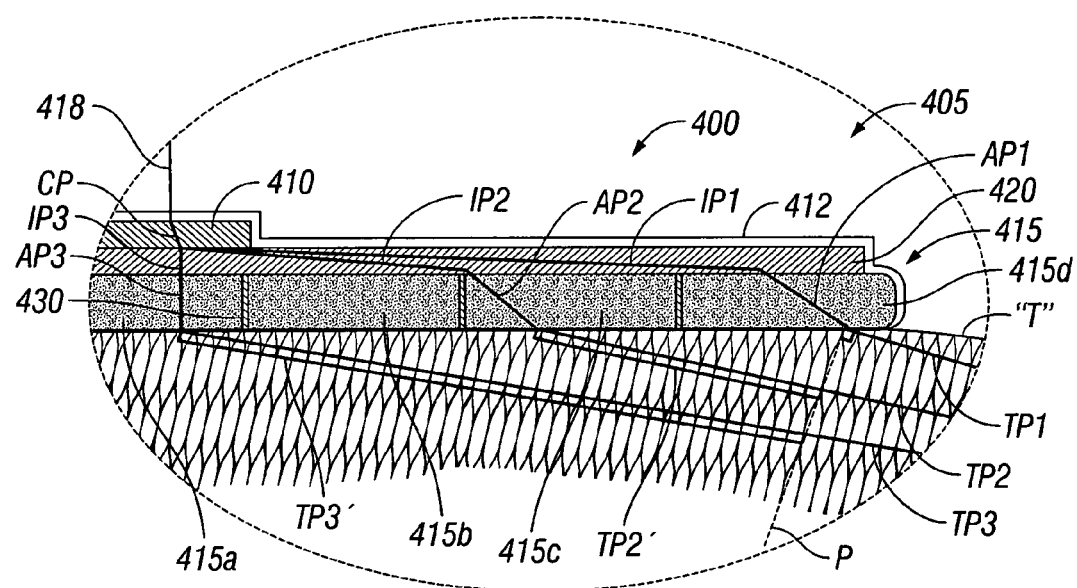
FIG. 4B is a cross sectional detail of the leading edge of the return pad of FIG. 4.

The size and placement of the conductive layer 310, relative to the intermediate layer 320 and contact layer 315, impacts the impedance of the various current pathways. Positioning conductive layer 310 substantially in the middle of the intermediate layer 320 and contact layer 315 effectively increases the impedance of the pathways at the edges of the return pad 350. As illustrated in FIGS. 4A and 4B, positioning conductive layer 410 away from the leading edge 405, increases the impedance of the pathways at the leading edge 405 of the return pad 400, thus further reducing the current density at the leading edge 405 of return pad 400.

Referring back to FIG. 3A, decreasing the size of the conductive layer 310 also increases the current density, and may result in the generation of heat at the connection between the intermediate layer 320 and the conductive layer 310.

Conductive layers 310, 410 may be formed as a single layer or may be formed as a plurality of sections separated by a barrier 330, 430, as illustrated in FIGS. 3A-3C and 4A-4C. Barrier 330, 430 may be formed from a conductive material or alternatively, as described hereinbelow, barrier 330, 430 may be formed from a non-conductive or insulating material.

Figure 3C:
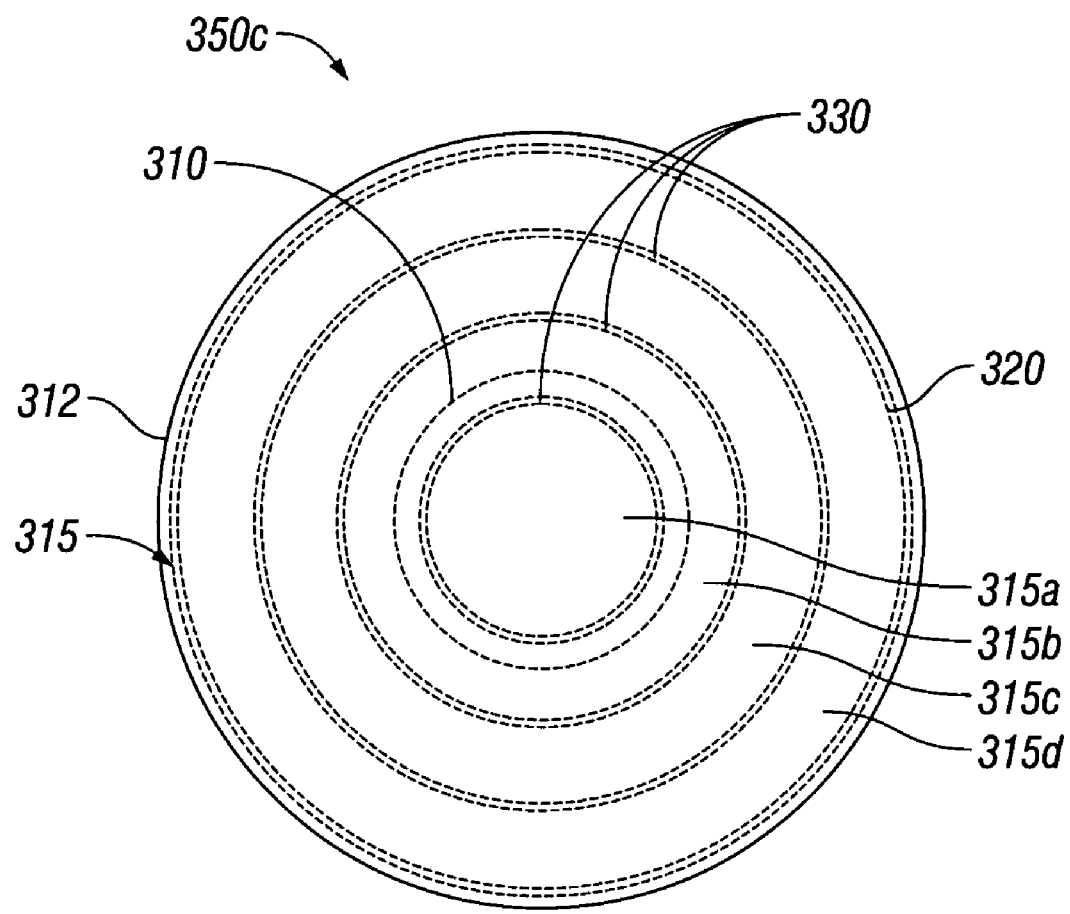
FIG. 3C is a top view of yet another embodiment of the return pad of FIGS. 3A-3B with an insulating barrier between the conductive gel portions.
Figure 4C:
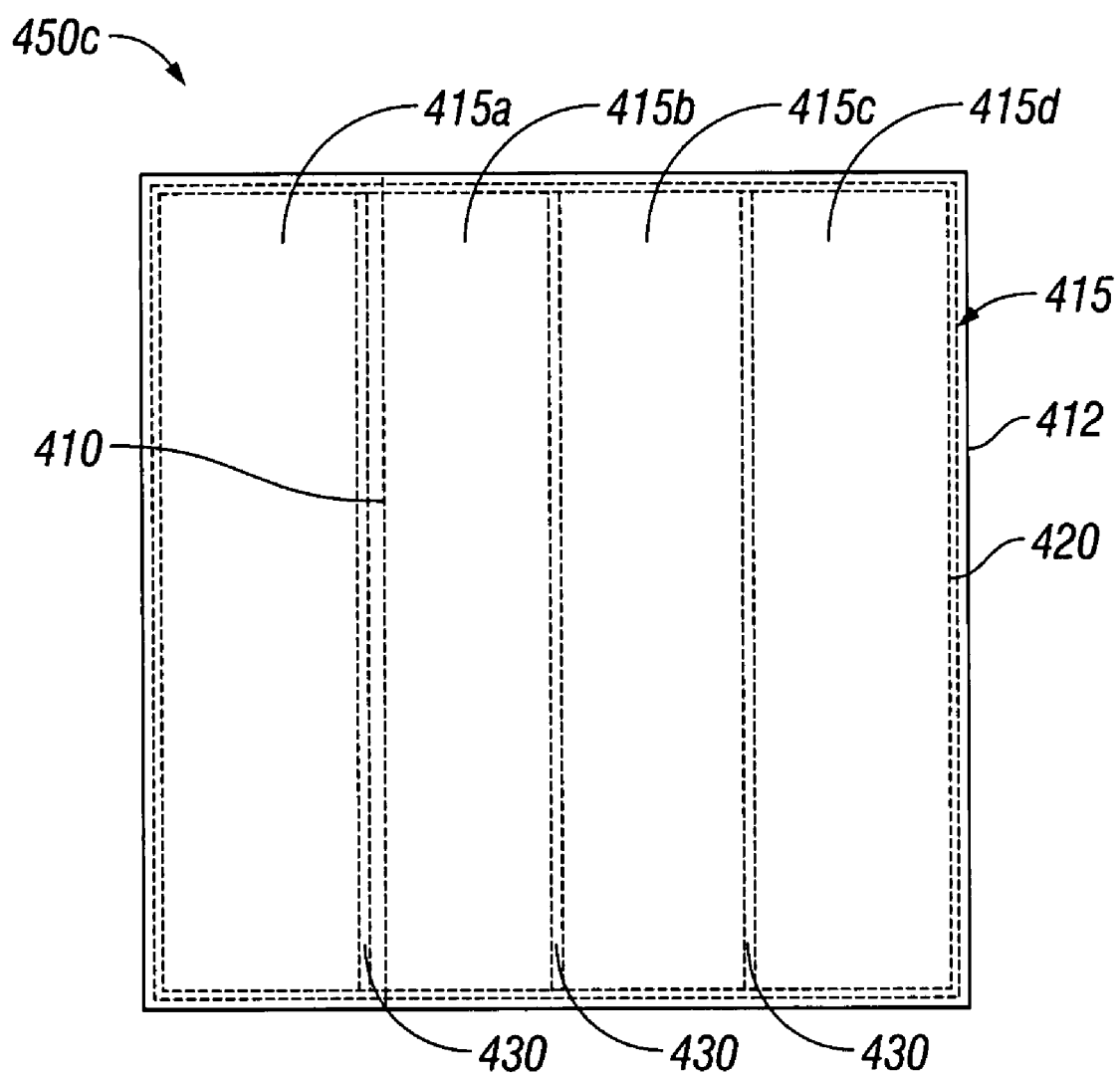
FIG. 4C is a top view of yet another embodiment of the return pad of FIGS. 4A-4B with an insulating barrier between the conductive gel portions.

In yet another embodiment of the present disclosure, as illustrated in FIGS. 3C and 4C, contact layer 315 includes a plurality of contact layer sections 315a-d, 415a-d formed as a plurality of concentric rings or rows. FIG. 3C illustrates a concentric or substantially circular return pad 350c, and FIG. 4C illustrates a rectangular shaped return pad 400c. Return pads 350c and 400c may be formed from any suitable shape, e.g., oblong, oval, hexagonal, or polygonal.

More particularly, FIG. 3C illustrates the return pad 350 of FIG. 3B with the various portions of the contact layer 315 separated by barriers 330 formed of a non-conductive or insulating material. Contact layer 315 includes a center contact portion 315c, a first contact ring 315b, a second contact ring 315c, and an outer contact ring 315d with a barrier 330 between the adjacent portions.

FIG. 4C illustrates the return pad 400 of FIG. 4B with various portions of the contact layer separated by barriers 430 formed of an insulating material. Contact layer 415 includes a first contact row 415a, a second contact row 415b, a third contact row 415c and an outer contact row 415d with a barrier 330 between the adjacent portions.

Barriers 330, 430 electrically isolate concentric rings 315a-d and rows 415a-d, respectively, thereby preventing current flow between rings 315a-d or rows 415a-d. Current enters the portion of the intermediate layer 320 above each concentric rings a-d or rows 415a-d. The current paths in contact layer 315 are substantially perpendicular to patient tissue "T" and the impedance of the intermediate paths will be different for each concentric ring 315a-d or rows 415a-d with the impedance of the pathways increasing as the distance away from the conductive layer 310 increases.

With reference to FIGS. 4A and 4B, leading edge 405 of return pad 400 is positioned closest to the active electrode (not explicitly shown) and conductive layer 410 is positioned away from leading edge 405. Current following the first tissue path (TP1) travels through outer contact row 415d, as illustrated by first contact path (AP1), and enters intermediate layer 415 toward the leading edge 405. Current travels across a substantial portion of the length of intermediate layer 415 as illustrated by first intermediate path (IP1), before entering conductive layer 410. Current following the third tissue path (TP3) travels through first contact row 415A, as illustrated by third adhesive path (AP3), and enters intermediate layer 415 in close proximity to conductive layer 410. Current must only travel across the width of intermediate layer 420 before entering conductive layer 410. For both examples, current takes a substantially similar path through conductive layer 410, as illustrated by conductive path CP.

In one embodiment, the intermediate layer 420 may be formed of material with impedance properties substantially similar to the impedance properties of patient tissue "T". Matching the impedance properties of the intermediate layer 420 to patient tissue "T" results in substantially similar impedance for any given path between the active electrode (not shown) and return cable 418 through the return pad 400.

With reference to FIGS. 3A, 3B, 4A and 4B, backing layer 312 and 412, respectively, is disposed upon at least a portion of conductive layer and intermediate layer.

Figure 5:
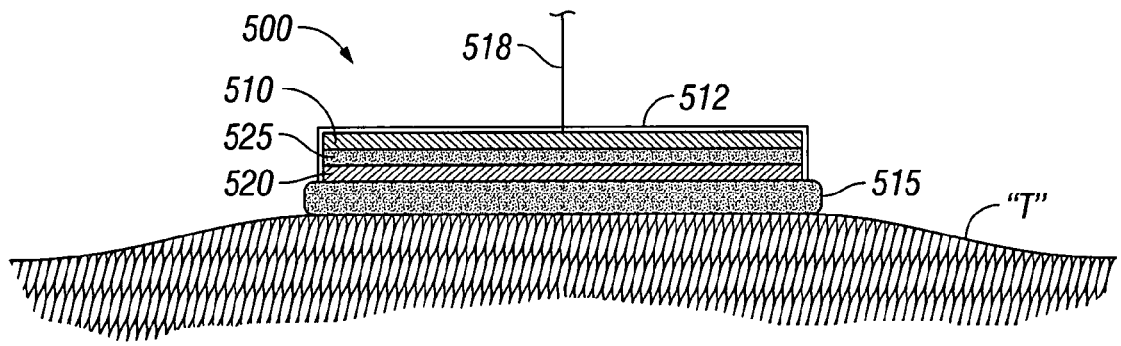
FIG. 5 is a cross-sectional view of a return pad with a plurality of contact layers.

FIG. 5 illustrates yet another embodiment of the present disclosure having a return pad 500 that provides, among other advantages, even heat and current distribution and is formed of a first contact layer 515 having a first side adapted to couple to patient tissue "T" and a second side adapted to couple to a first side of intermediate layer 520. A second contact layer 525 engages second side of intermediate layer 520 to conductive layer 510. First and second contact layer can be made from, but is not limited to, a polyhesive adhesive, conductive hydrogel, a Z-axis adhesive or a water-insoluble, hydrophilic, pressure-sensitive adhesive. Insulating layer 512 is disposed upon the top portion of conductive layer 510 and return cable 518 connects to conductive layer 510.

Return Pad Cooling

Figure 6A:
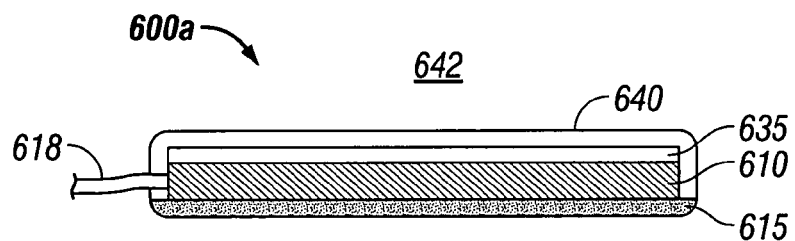
FIG. 6A is a cross sectional view of a return pad with a passive cooling layer.

With reference to FIG. 6A, a cooled return pad 600a is shown and includes a contact layer 615, a conductive layer 610, a cooling layer 635 and a backing layer 640. Return cable 618 connects to conductive layer 610, which is formed of a suitable metal foil, dielectric material or dielectric/metal material combination. Cooling layer 635 and conductive layer 610 are configured in thermal communication such that energy, e.g., heat, is distributed and/or dissipated. Distribution and/or dissipation (herein referred to as distribution) of energy includes the transfer of energy between patient skin and/or the layers of the return pad 600a, the transfer of energy from the return pad to the surrounding area 642 and/or the transfer of energy between conductive layer 610 and cooling layer 635. Cooling layer 635 may be formed of an electrically non-conductive material and/or may be electrically isolated from conductive layer 610.

Cooling layer 635 may employ passive or active cooling techniques. Passive cooling requires backing layer 640 to be formed from a breathable material that allows heat to dissipate from cooling layer 635 into surrounding area 642. Active cooling may require backing layer 640 to be formed of impervious material to facilitate circulation of a cooling air or fluid. Backing layer 640 may form an air-tight or liquid-tight seal with conductive layer 610 or other portion of return pad 600a.

Figure 6B:
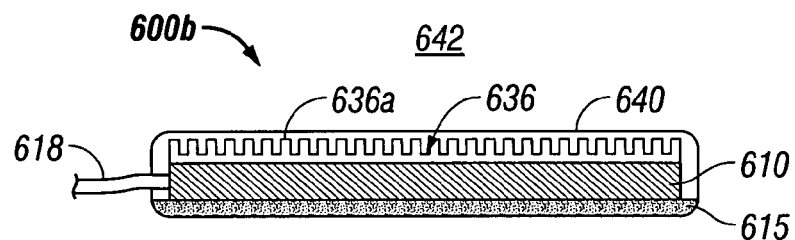
FIG. 6B-6E illustrate various embodiments of passive cooling layers.

FIGS. 6B-6E illustrates several constructions of a cooled return pad with passive cooling. FIG. 6B illustrates cooled return pad 600b with a backing layer 640, contact layer 615, conductive layer 610, a return cable 618 connected to conductive layer 610 and a heat exchanger 636 as the cooling layer. Heat exchanger 636 may include a plurality of fins 636a to aid in the dissipation of heat. Heat exchanger 636 may be formed of any heat conducting material provided heat exchanger 636 is electrically isolated from conductive layer 610. Heat exchanger 636 may be formed of a heat conducting insulator, such as, for example a ceramic or dielectric material. Backing layer 640 is disposed on or otherwise integrated with heat exchanger 636 and is formed of highly permeable material that allows heat to dissipate or exchange with surrounding area 642.

Figure 6C:
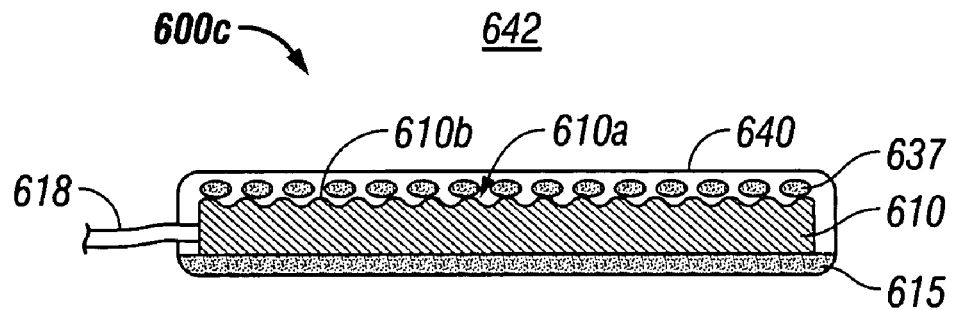

FIG. 6C shows yet another embodiment of the present disclosure having the cooling layer as an evaporative layer 637. Cooled return pad 600c includes evaporative layer 637 formed of a liquid or semi-liquid material with highly evaporative properties, such as, for example, alcohol or water, or alcohol or water-based gel. Evaporative layer 637 absorbs heat from conductive layer 610 and heat is removed from cooled return pad 600c by evaporation, i.e. vaporization or evaporation of the evaporative material in evaporative layer 637. Top surface 610a of conductive layer 610 may form ridges or fins 610b to increase the area of contact surface between conductive layer 610 and evaporative layer 637. Backing layer 640 is permeable to air. Alternatively, backing layer 640 may be permeable to air and impermeable to the material forming the evaporative layer 637. Backing layer 640 contains evaporative layer 637 between backing layer 640 and conductive layer 610 while allowing the vaporized gas to remove the heat. Backing layer 640 may be formed of a cloth or fabric treated with thermo-mechanically expanded polytetrafluoroethylene (PTFE) or other Fluoropolymer, such as the fabric treatment commonly sold over the trademark Gore-Tex™ or other porous hydrophobic materials or coating.

Figure 6D:
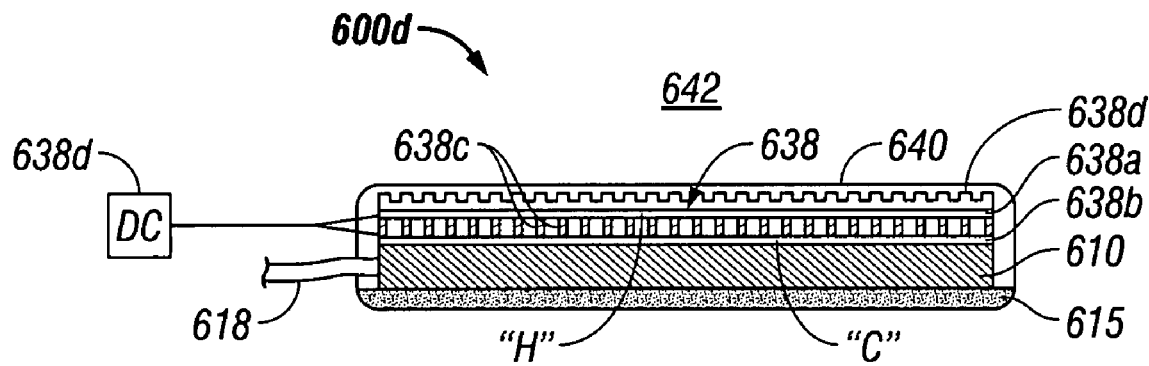

FIG. 6D shows yet another embodiment of the present disclosure having the cooling layer of the cooled return pad 600d composed of one or more Peltier devices 638, a well known device in the art that operates as a heat pump. In one embodiment, Peltier device 638 is formed by sandwiching a series array of small p and n type Bismuth Telluride cubes 638c between two metallized ceramic plates 638a and 638b that connect the cubes in series and applying a DC current, supplied from a DC power supply 638D, thereto. When a DC current is applied to the series array of small Bismuth Tellurite cubes 638c, heat moves from one side of the Peltier device 638 to the other. The cold side "C" cools the conductive layer 610 and the contact layer 610 and the hot side "H" exchanges heat with the surrounding air 642. Peltier device 638 may also include a heat sink 638d to improve the cooling effect. Backing layer 640 is disposed on Peltier device 638 and is formed of highly permeable material that allows heat to dissipate or exchange with surrounding air 642.

Figure 6E:
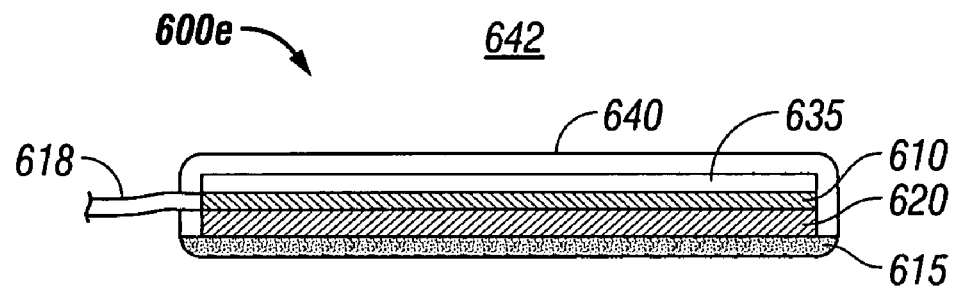

FIG. 6E illustrates another embodiment of the present disclosure having a cooled return pad 600e with even heat distribution. More particularly, return pad 600e includes an intermediate layer 620, as illustrated in FIGS. 1-5 and disclosed hereinabove, and a cooling layer 635 as illustrated in FIGS. 6A-6D and 7-9 and discussed herein. Intermediate layer 620 provides even current and hence even heat distribution and dissipation of energy and cooling layer 635 removes heat from the return pad 600e.

Cooled return pad 600e includes a backing layer 640, a cooling layer 635, a conductive layer 610, an intermediate layer 620 and a contact layer 615. Conductive layer 610 is disposed between intermediate layer 620 and cooling layer 635. Intermediate layer 620 is disposed between conductive layer 610 and contact layer 615. Backing layer 640 is disposed upon at least a portion of cooling layer 635 and allows heat to dissipate or exchange with the surrounding air 642.

While FIGS. 6B-6E illustrate various passive techniques of cooling a return pad, other suitable techniques of passive cooling may be used. Moreover, a passive cooling technique may be combined with one or more active cooling techniques as disclosed below.

Figure 7:
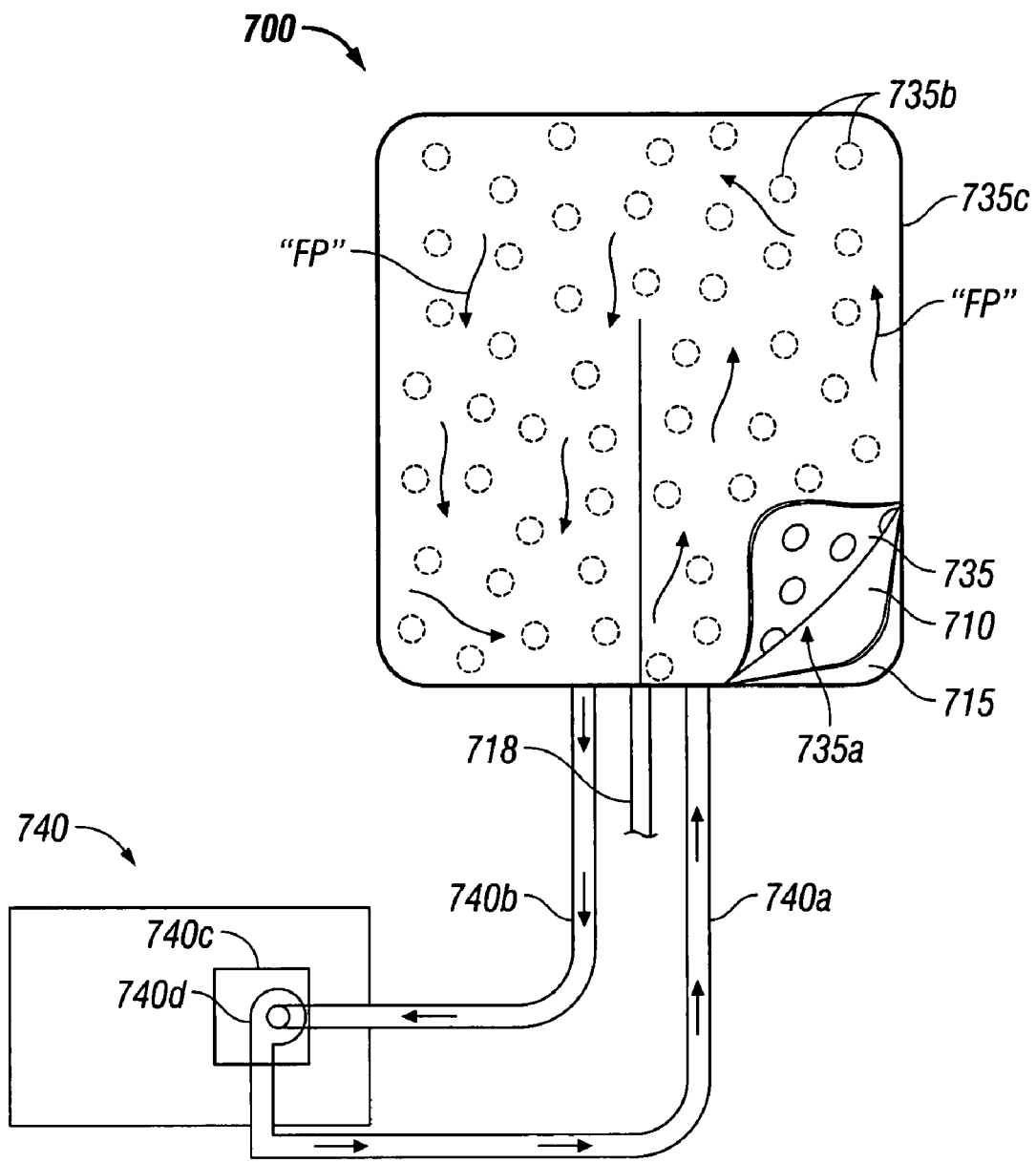
FIG. 7 is a top view of a return pad with an active cooling system.

With reference to FIG. 7, cooled return pad 700 includes a contact layer 715, a conductive layer 710, a return cable 718 connected to conductive layer 710 and a backing layer 735. Backing layer 735 and conductive layer 710 form a cooling chamber 735a for circulating cooling fluid therewithin. Cooling chamber 735a may be further defined by dimples 735b on backing layer 735. Dimples 735b are configured as spacers between contact conductive layer 710 backing layer 735 and provide cooling chamber with support and dimension. Edge 735c provides a seal between the layers forming the cooling chamber 735a and contains cooling fluid within cooling chamber 735a. Seal may be formed mechanically, i.e. clamping, crimping, etc., or by bonding, i.e. adhesive, ultrasonic bonding, etc, or by other suitable sealing techniques.

Alternatively, dimples 735b may be formed by point or spot welding the layers that from the cooling chamber 735a. Cooling chamber 735a defines one or more fluid pathway "FP". Pump 740d supplies cooling fluid to inflow tube 740a, cooling fluid circulates through cooling chamber and outflow tube 740b returns cooling fluid to cooling system 740.

Cooling chamber 735a may also be defined by one or more channels formed in the backing layer 735 and/or conductive layer 710. Cooling chamber may be a single channel or chamber or may comprise a plurality of channels or chambers.

Cooling fluid may be purified water, distilled water or saline, although any suitable fluid, including air, may be used. Cooling system may also include a cooling module 740c, such as a refrigeration system, one or more Peltier device, vortex cooling device, heat exchanger, ice, etc. While FIG. 7 illustrates an active cooling technique for a return pad 700, other suitable active cooling techniques art may be utilized to accomplish the same purpose.

Figure 8:
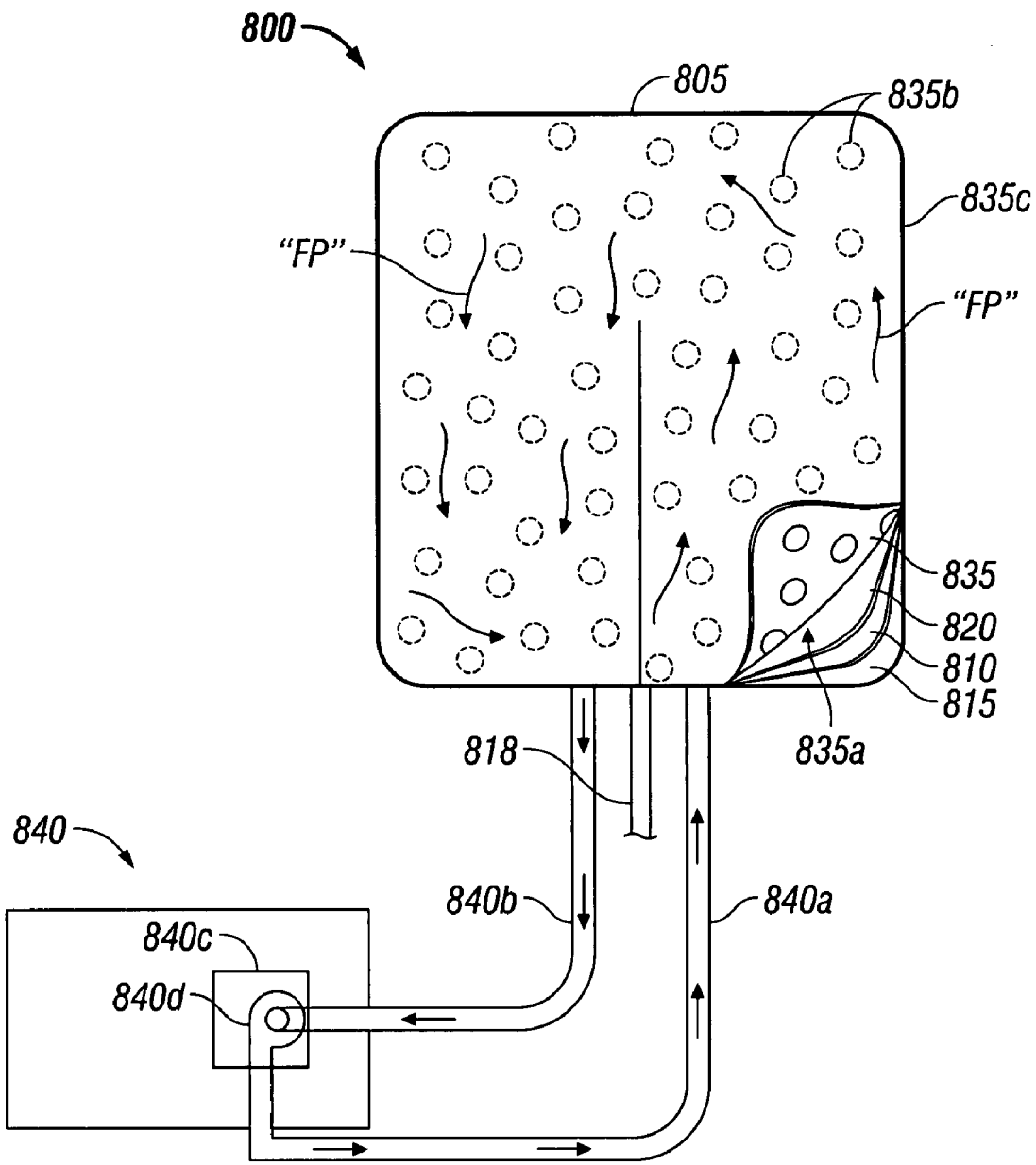
FIG. 8 is a top view of the return pad of FIG. 7 with an even heat distribution layer.

FIG. 8 shows a cooled return pad 800 that includes an intermediate layer 820 to provide even heat distribution as disclosed hereinabove. While many different variations and combinations are envisioned, FIG. 8 illustrates a particular embodiment with the even heat distribution pad, illustrated in FIGS. 4A and 4B and disclosed hereinabove, incorporated into the cooled return pad 700 illustrated by FIG. 7 and described hereinabove.

Return pad 800 includes a contact layer 815, a conductive layer 810, an intermediate layer 820, and a cooling layer 835. Conductive layer 810 is disposed on intermediate layer 820. Alternatively, conductive layer 810 may be disposed on only a portion of intermediate layer 820. As discussed hereinabove, the size and placement of the conductive layer 810 relative to the leading edge 805 of the pad 800 effects the impedance of the various current paths. Dimples 835b contact conductive layer 810 and/or intermediate layer 820 and provide cooling chamber with support and dimension and define various fluid pathways "FP" in cooling chamber 835a. Pump 840d supplies cooling fluid to inflow tube 840a and outflow tube 840b returns cooling fluid to cooling system 840. Cooling module 840a may include a refrigeration system, a Peltier device, a vortex cooling device, a heat exchanger, ice, etc.

As disclosed hereinabove, intermediate layer 820 reduces the current density at the leading edge 805 of cooled return pad 800, dissipates energy and/or conveys heat from hot spots thus providing even heat distribution across the cooled return pad 800. Even distribution of heat across the cooled return pad 800 enables cooling system 840 to more efficiently remove heat and reduce the temperature of cooled return pad 800.

Seal along edge 835c is formed between conductive layer 810 and backing layer 835, and between intermediate layer 820 and backing layer 835. Cooling chamber 835a, formed between backing layer 835 and at least a portion of conductive layer 810 and a portion of intermediate layer 820, is configured to allow fluid to flow therethrough. Seal along edge 835c may be formed mechanically, i.e. clamping, crimping, etc., or by bonding, i.e. adhesive, ultrasonic bonding, etc, or by other suitable sealing technique. Cooling chamber 835a may be formed over intermediate layer, conductive layer or both.

Figure 9:
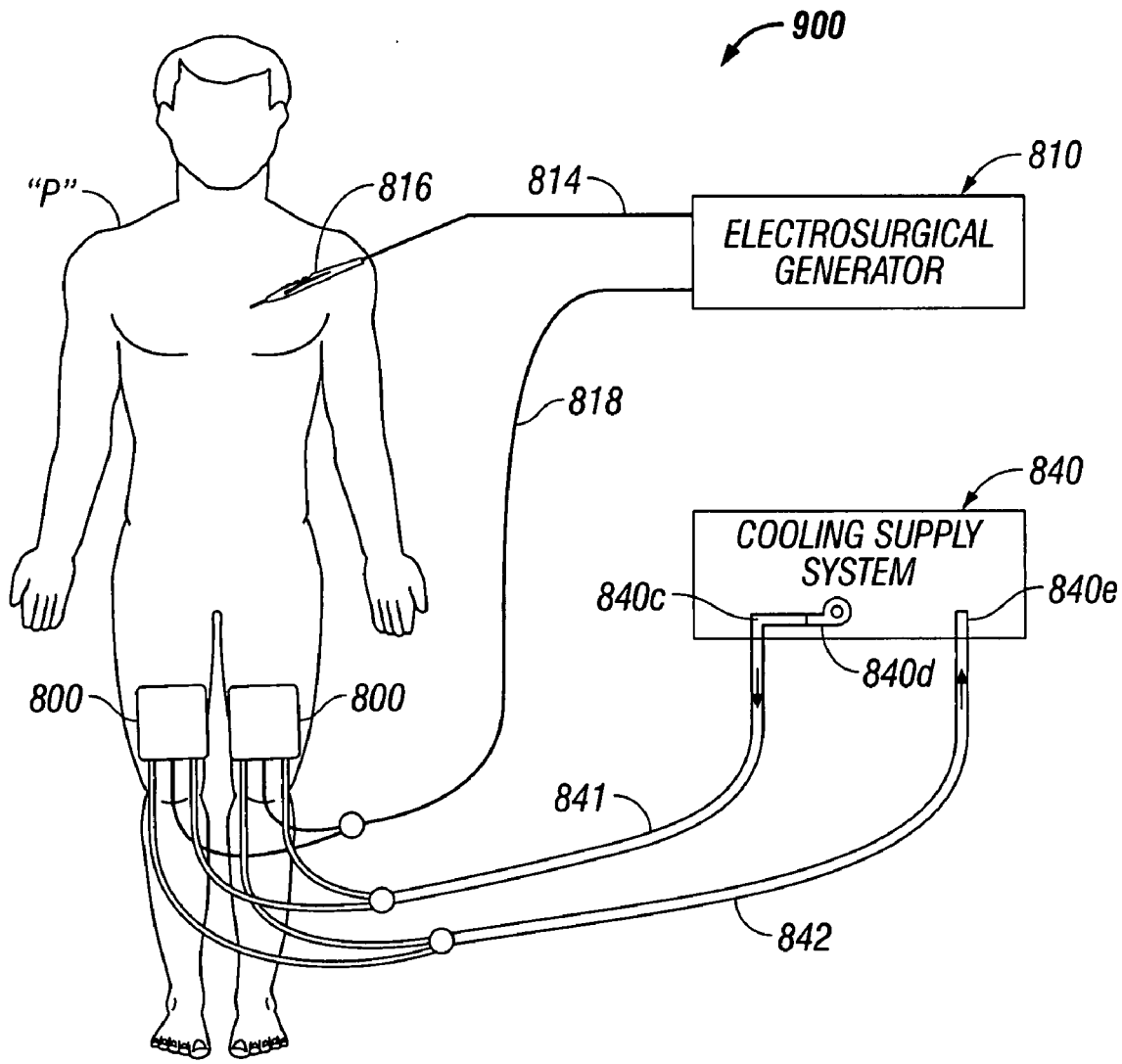
FIG. 9 is a cross-sectional view of yet another embodiment of an active cooling system with an intermediate layer.

FIG. 9 illustrates an electrosurgical system 900 including an electrosurgical generator 810, an active electrode 816, a cooled return pad 800 and a cooling fluid supply system 840. Electrosurgical generator 810 supplies electrosurgical energy to active electrode 816 through supply cable 814 and return pads 800 returns electrosurgical energy to electrosurgical generator 810 through return cable 818. Return cable 818 may also supply power DC power from the electrosurgical generator to cooling device in the return pads 800.

Cooling supply system 840 includes a cooling supply tube 841 that connects to a cooling supply 840c, a cooling return tube 842 that connects to the cooling return 840e and a pump 840d. In one embodiment, pump 840d supplies cooling fluid to the cooled return pads 800 through cooling supply 840 and cooling fluid supply tube 841. Cooling fluid from the return pad 800 then returns to cooling system 840 through cooling fluid return tube 842 and cooling return 840e. Cooling supply system 840 may use any suitable supply for the cooling fluid, such as, for example, a saline drip bag or potable water supply. Cooling supply system 840 may circulate fluid thus relying on the ambient temperature to cool the fluid or cooling system supply 840 may include a variety of mechanism that are designed to cool the fluid, such as, for example, a refrigeration unit, a Peltier device, a heat exchanger, etc.

In use, a clinician connects supply cable 814 of electrosurgical return pad 800 to electrosurgical generator 810 and places return pad 800 in contact with patient "P" skin. Cooling device on return pad 800 may be connected to an energy supply such as, for example, an electrical energy source (not shown) or a cooling fluid supply system 840. An active cooling layer or device on return pad 800 may be enabled by providing electrical power or cooling fluid flow. A passive cooling device or layer may be enabled by exposing the device or layer to ambient air. Electrosurgical generator 810 generates electrosurgical energy and supplies the electrosurgical energy to the patient via an active electrode 816.

Return pad 800 in electrosurgical system 900 may include one or more the above identified features in any of the embodiments of the present disclosure.

In yet another embodiment, cooling supply system 840 may include one or more chemicals that actively cool the return pads 800 in which the one or more chemicals may react to cool the return pads 800. For example, cooling supply tube 841 may include two lumens and may supply two fluids that create an endothermic reaction when released and combine in the cooling chamber. Cooling supply system may use other suitable methods of chemical cooling the return pad 800.

Return Pad Heating

Figure 10A:
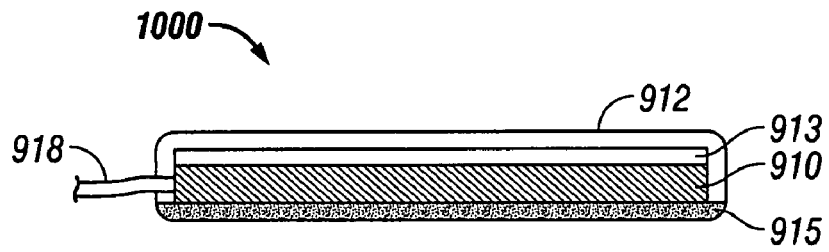
FIG. 10A is a cross-sectional view of yet another embodiment of a return pad with a heating layer.
Figure 10B:
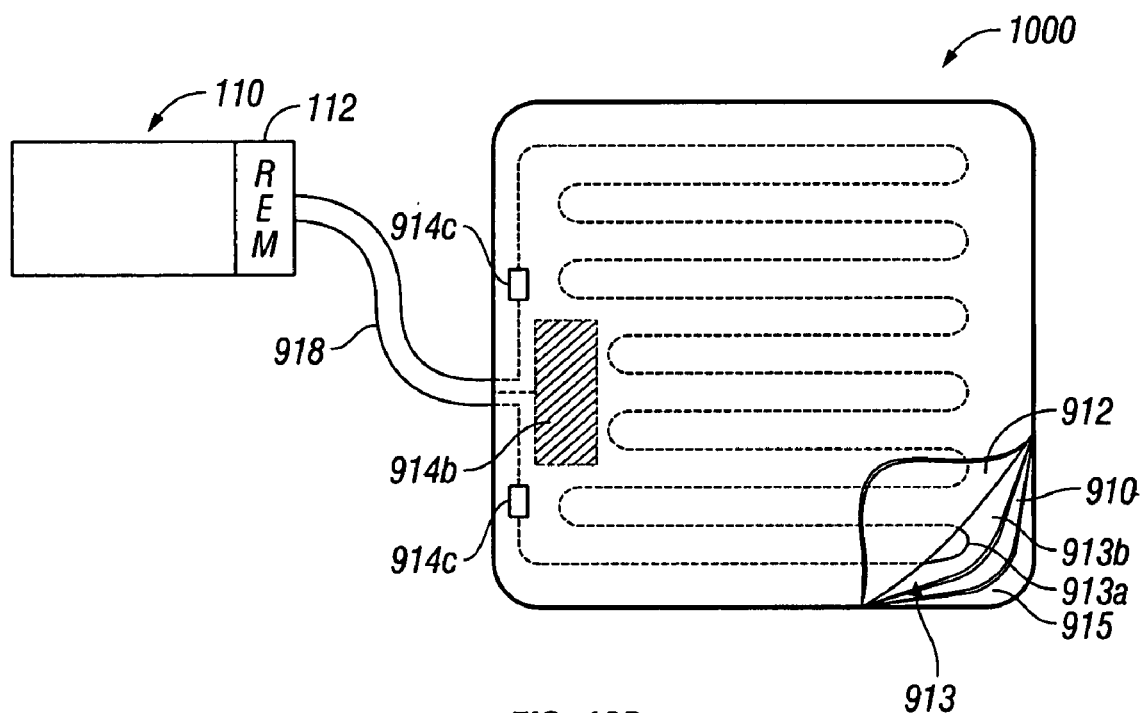
FIG. 10B is a top view of the return pad of FIG. 10A wherein the heating layer utilizes an electric heater.
Figure 10C:
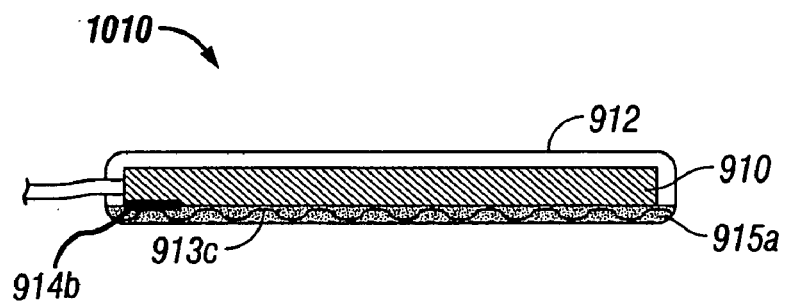
FIG. 10C is a cross-sectional view of a return pad with the heating layer disposed in at least a portion of the contact layer.

FIGS. 10A-10C illustrate other embodiments of the present disclosure having heated return pads 1000, 1010. Heated return pads 1000, 1010 are configured in such a manner that the return pads are heated either prior to or after applying the return pad to a patient.

With reference to FIG. 10A, heated return pad 1000 includes a heating layer 913 for heating at least a portion of the return pad 1000. As discussed hereinbelow, heating layer 913 may be an active heating layer, e.g., an electric heating means, or heating layer 913 may be a passive heating layer, e.g., one or more materials that create an exothermal chemical reaction. One purpose of the heating layer 913 is to preheat at least a portion of the contact layer 915 to a temperature similar to the temperature of patient's skin, typically between about 30° C. and 35° C., thus eliminating or reducing patient discomfort that may be associated with adhering a cold return pad 1000 to patient's skin.

Heated return pad 1000 also includes a contact layer 915, a conductive layer 910, and a backing layer 912. A cable 918 connects to conductive layer 910 and, in some embodiments, may connect to heating layer 913. The composition and function of contact layer 915, conductive layer 910, and backing layer 912 are described hereinabove. Heating layer 913, as described hereinbelow may be incorporated into any of the embodiments described herein or any combination of embodiments.

Heating layer 913 may be in thermal communication with contact layer 915 through conductive layer 910, as illustrated in FIG. 10A. Conductive layer 910 thermally conducts heat energy generated by the heating layer 913 from heating layer 913 to contact layer 915. Alternatively, at least a portion of heating layer 913 may be in direct contact with the contact layer 915 and thereby directly heat contact layer 915. In yet another embodiment, such as is illustrated in FIG. 10C, heating layer 913 may be at least partially positioned within contact layer 915 or the functionality of the heating layer 913 may be incorporated into contact layer 915.

FIG. 10B is a top view of the return pad 1000 of FIG. 10A (shown disposed within the active heating layer 913) and includes an electric heater element 913a and a substrate 913b. Electric heater element 913a may be disposed on substrate 913b or heater element 913a may be disposed between two substrates. One example of a suitable heater is a thermofoil heater manufactured by Minco under the trademark Kapton™. Substrate 913b may electrically insulate heater element 913a from conductive layer 910 while allowing heat energy to transfer from heating layer 913 to conductive layer 910.

Cable 918 is configured to supply electric current to heater element 913a from the electrosurgical generator or other suitable power source. Heater element 913a may also be a resistive-type heater and may be powered with AC or DC current. For example, heater element 913a may be powered by the electrosurgical generator 110 with a frequency of about 500 kHz, 120 VAC or 50 VDC.

Various types of heaters could be used for the heating layer 913 provided the heater is sufficiently thin and insertable into return pad 1000 and/or sufficiently flexible as to not add an appreciable amount of stiffness to the return pad 1000. Heater element 913a (when disposed within the heater) may be formed from a single element, as illustrated in FIG. 10B, or heater may be formed with several heater elements arranged in parallel. For example, the thermofoil heater manufactured by Minco under the trademark Kapton™ has a suitable thickness of approximately 7 mils.

In yet another embodiment, as illustrated in FIG. 10C, heating element 913b is at least partially disposed in at least a portion of contact layer 915a and performs the function of the heating layer 913 in FIGS. 10A and 10B. Conductive layer 910 is disposed between the backing layer 912 and the contact layer 915.

Again with reference to FIG. 10A, other technologies may be employed to perform the same or similar functions as heating layer 913. For example, a chemical, exothermic pack (not shown) may be used to generate a sufficient amount of energy to heat the contact layer 915 to a target temperature. Exothermic pack may be manually activated, automatically activated when connected to the electrosurgical generator or activated when the return pad is removed from the packaging.

In operation of one embodiment, heating layer 913 preheats the contact layer 915 prior to the application of the return pad 1000 to a patient's skin. The contact layer 915 is pre-heated to a temperature about equal to, or slightly less than, the surface temperature of skin to prevent patient discomfort that may be experienced when the contact layer 915, at room temperature, or approximately 22° C., is placed on skin at the body temperature, or approximately 35° C.

Heating layer 913 is capable of providing a sufficient amount of energy to heat contact layer 915 to a target temperature. The target temperature may vary based on the specific application and use. For example, the target temperature may range from 30° C. to 35° C. for application and use on a human and the upper limit may be as high as 39° C. for veterinarian use.

The energy delivered by the heating layer 913, e.g., the rate of power delivered and/or the total amount of energy delivered, may be specifically matched to the size and/or volume of contact layer 915. For example, to heat and maintain a 3×3 inch return pad at a target temperature may require a lower rate of energy delivery and less total energy than what may be required to heat and maintain a 4×4 inch return pad.

The rate of power delivery and/or the total amount of energy delivered can be easily calculated if the energy source is chemical, such as, for example, an exothermic pack. The exothermic pack may only last for a few minutes and may provide a sufficient amount of heat energy to heat the contact layer 915 to the target temperature. The heating capacity of the exothermic pack may be varied to match the size and/or volume of the contact layer 915.

A heating layer 913 that receives energy from an electrical energy source may require one or more safety features to ensure that the temperature of the contact layer 915 does not exceed a target temperature. For example, with reference to FIGS. 10B and 10C, temperature sensor 914b may be used to measure the temperature of the return pad. An electrical energy source, e.g., the electrosurgical generator 110, then controls the current to heating layer 913 to maintain return pad 1000 at a target temperature.

Various safety measures may be employed to insure that heating layer 913 does not overheat heated return pad 1000. For example, one or more devices 914c may be incorporated in or associated with heating element 913a to interrupt or limit the current supplied to the heating element 913b. Device 914a may be a current limiting fuse, a thermal cut-off device, a timer-type device or any suitable device that may be incorporated into the circuit and/or system to prevent the return pad 1000 from exceeding the target temperature range.

Other safety measures may be incorporated into the electrosurgical generator 110. For example, electrosurgical generator 110 may employ existing circuitry to measure the temperature of the return pad or to measure the amount of current supplied to the heating element 913a. Electrosurgical generator 110 may terminate the supply of current when a predetermined temperature is obtained or after a predetermined amount of energy is supplied to the return pad 1000. Alternatively, new hardware and/or new software may be incorporated into the electrosurgical generator 110 to detect when a return pad 1000 is initially connected to the electrosurgical generator. Connecting the return pad 1000 may cause the electrosurgical generator 110 to automatically heat the return pad 1000 for a predetermined period of time or until a predetermined amount of energy is delivered to the return pad 1000. The predetermined period of time and predetermined amount of energy may be determined by the clinician or electrosurgical generator 110 may be configured to automatically determine or calculate the period of time based on the size and/or type of return pad.

Current supplied to the heating element 913a may be terminated when the electrosurgical generator 110 detects that the return pad 1000 is in contact with tissue. The return electrode monitor (REM) 112, or any other suitable contact quality system, may be used to determine when the return pad 1000 is in contact with patient tissue.

In use, return pad 1000 is connected to the electrosurgical generator 110. Electrosurgical generator 110 automatically switches power to heater element 913a and supplies a low level current. Current is limited to an amount that will heat the return pad 1000 to a target temperature without resulting in an over-temperature condition. At least periodically, the REM 112 may be activated to determine if the return pad 1000 is applied to patient. After contact current to the heater element 913a is switched off, the return pad 1000 is enabled and the system is ready for activation. If temperature sensor 913b is present, temperature at the return pad 1000 may be measured and the current to the heater element 913a may be automatically adjusted by the electrosurgical generator 110 to maintain return pad 1000 at a target temperature. Safety devices 914c, if present, may disable the current flow if the return pad 1000 exceeds a maximum temperature.

In an alternative application, a heating layer, such as heating layer 913, may be employed on the back of a return electrode that could be used for patient heating. Typically, patients are kept warm with blankets and/or water or air flow heating systems. According to an embodiment of the disclosure, a large surface area pad, constructed with a backing layer, a thermofoil heater(s), and an adhesive hydrogel could provide a low profile solution to patient heating. The adhesive hydrogel may provide a uniform and comfortable contact area. Temperature sensing devices, such as thermistors or thermocouples, may be included in such a system to regulate temperature and ensure that the pad does not get too warm.

While several embodiments of the disclosure have been shown in the drawings, it is not intended that the disclosure be limited thereto, as it is intended that the disclosure be as broad in scope as the art will allow and that the specification be read likewise. For example, the return pad may include a plurality of electrodes or may include a plurality of novel intermediate layers. Therefore, the above description should not be construed as limiting, but merely as exemplifications of various embodiments. Those skilled in the art will envision many other possible variations that are within the scope and spirit of the disclosure as defined by the claims appended hereto.

What is claimed is:

1. A return pad for use with an electrosurgical system, comprising:
   a conductive layer;
   a contact layer disposed on the conductive layer and configured to engage patient skin;
   a cooling section disposed on the conductive layer and configured to reduce the temperature of at least one of the contact layer and the conductive layer; and
   a backing layer disposed on the cooling section and adapted to allow heat to dissipate therethrough,
   wherein the conductive layer, contact layer and cooling section are substantially coterminous.

2. The return pad according to claim 1, wherein the cooling section is configured to absorb thermal energy generated in the return pad.

3. The return pad according to claim 1, wherein the cooling section is configured to absorb thermal energy from the conductive layer and the contact layer.

4. The return pad according to claim 1, wherein the cooling section includes a passive cooling device.

5. The return pad according to claim 1, wherein the cooling section includes a Peltier cooling device.

6. The return pad according to claim 1, wherein the cooling section includes a chemical layer.

7. The return pad according to claim 6, wherein the backing layer is permeable to air and impermeable to the chemical layer.

8. The return pad according to claim 1, wherein the backing layer is includes a breathable material that is configured to allow thermal energy from the cooling layer to dissipate therethrough and into the surrounding area.

9. The return pad according to claim 1, wherein the backing layer includes an impervious material that forms one of an air-tight seal and a liquid-tight seal with the conductive layer.

10. The return pad according to claim 9, wherein the backing layer facilitates circulation of a fluid.

11. The return pad according to claim 9, wherein the backing layer and the conductive layer form a cooling chamber configured to circulate cooling fluid therewithin.

12. The return pad according to claim 11, wherein the cooling chamber is further defined by a plurality of dimples formed on the backing layer.

13. The return pad according to claim 11, wherein the cooling chamber is further defined by one or more channels formed in the backing layer.

14. The return pad according to claim 11, wherein the cooling chamber is further defined by one or more channels formed in the conductive layer.

15. The return pad according to claim 1, wherein the cooling section further includes a heat exchanger and the backing layer is formed of highly permeable material that is configured to allow thermal energy to dissipate to the surrounding area.

16. The return pad according to claim 1, wherein the backing layer is treated with a thermo-mechanically expanded polytetrafluoroethylene.

17. The return pad according to claim 1, wherein the backing layer is a porous hydrophobic material.

* * * * *